US008571801B2

(12) United States Patent
Anfinsen et al.

(10) Patent No.: US 8,571,801 B2
(45) Date of Patent: Oct. 29, 2013

(54) METHODS AND SYSTEMS FOR DETERMINING AND CONTROLLING GLYCEMIC RESPONSES

(75) Inventors: Jon R Anfinsen, Alachua, FL (US);
Thomas Wolever, Toronto (CA);
Matthew Spolar, Brooklyn, NY (US);
Elinor Hitchner, Morristown, NJ (US);
Paul D. Wolff, Easton, CT (US)

(73) Assignee: Atkins Nutritionals, Inc., New York, NY (US)

( * ) Notice: Subject to any disclaimer, the term of this patent is extended or adjusted under 35 U.S.C. 154(b) by 1617 days.

(21) Appl. No.: 11/368,297

(22) Filed: Mar. 3, 2006

(65) Prior Publication Data

US 2006/0154322 A1 Jul. 13, 2006

Related U.S. Application Data

(62) Division of application No. 10/229,952, filed on Aug. 28, 2002, now abandoned.

(51) Int. Cl.
*G01N 33/48* (2006.01)
*C12Q 1/00* (2006.01)

(52) U.S. Cl.
USPC .................................................. 702/19; 435/5

(58) Field of Classification Search
None
See application file for complete search history.

(56) References Cited

U.S. PATENT DOCUMENTS 5,691,927 A 11/1997 Gump
6,040,531 A 3/2000 Miller-Kovach et al.

FOREIGN PATENT DOCUMENTS

WO WO 97/02050 1/1997
WO WO 01/91633 12/2001
WO WO 02/11562 2/2002

OTHER PUBLICATIONS

Holt, et al. "The Effects of Equal-Energy Portions of Different Breads on Blood Glucose Levels, Feelings of Fullness and Subsequent Food Intake," *Journal of the American Dietetic Association*, 101:767-773 (2001).
Hertzler et al., "Glycemic Index of 'Energy' Snack Bars in Normal Volunteers," *Journal of the American Dietetic Association*, 100(1):97-100 (2000).
Foster-Powell et al., "International table of glycemic index and glycemic load values: 2002," *American Journal of Clinical Nutrition*, 76:5-56, p. 5-56.
Brody, Jane E., "Fear not that Carrot, Potato or Ear of Corn," *The New York Times*, (Jun. 11, 2002).
Liu et al. "A prospective study of dietary glycemic load, carbohydrate intake, and risk of coronary heart disease in US women," *American Journal of Clinical Nutrition*, 71:1455-61 (2000).
Christensen et al., "Significance of Glucose Load in Oral Glucose Tolerance Tests," *Acta Med. Scand.*, 192:337-342 (1972).
Jourdan, M.H., "The Influence of Different Amounts and Concentrations of Glucose on the Oral Glucose Tolerance Test," Department of Physiology, Guy's Hospital Medical School, London SE1 9RT, p. 155-162.
Wolever, Thomas MS, "The use of the glycemic index in predicting the blood glucose response to mixed meals," *The American Journal of Clinical Nutrition*, 43:167-172 (1986).
Wolever et al., "The Glycemic Index: Variation Between Subjects and Predictive Difference," *Journal of the American College of Nutrition*, 8(3):235-247 (1989).
Ford et al. "Glycemic Index and Serum High-Density Lipoprotein Cholesterol Concentration Among US Adults," Arch. Intern. Med., 161:572-576 (2001).
Holt et al., "Interrelationships Among Postprandial Satiety, Glucose and Insulin Responses and Changes in Subsequent Food Intake," *European Journal of Clinical Nutrition* 50:788-797(1996).
Brand et al., "Low-Glycemic Index Foods Improve Long-Term Glycemic Control in NIDDM," *Diabetes Care*, 14(2):95-101 (1991).
Rickard et al., "Similar Glycemic Responses to High Versus Moderate Sucrose-Containing Foods in Test Meals for Adolescents with Type 1 Diabetes and Fasting Euglycemia," *Journal of the American Dietetic Association*, 101(10):1203-1205 (2001).
Wolever et al. "Prediction of the Relative Blood Glucose Response of Mixed Meals Using the White Bread Glycemic Index," *Diabetes Care*, 8(5):418-428 (1985).
Wolever et a., "The Glycemic Index: Methodology and Clinical Implications," *American Journal of Clinical Nutrition*, 54:846-54 (1991).
Brand, J. et al., "Food Processing and the Glycemic Index," *The American Journal of Clinical Nutrition*, 42:1192-1196 (1985).
Jenkins et al., "Glycemic Index of Foods: A Physiological Basis for Carborhydrate Exchange," *The American Journal of Clinical Nutrition*, 34:362-366 (1981).
Lee et al., "Effect of Glucose, Sucrose and Fructose on Plasma Glucose and Insulin Responses in Normal Humans: Comparison with White Bread", Department of Nutritional Science, University of Toronto, p. 924-927 (1998).
Foster-Powell et al., "International Tables of Glycemic Index," *American Journal of Clinical Nutrition*, 62:871S-93S (1995).
Wolever et al., "Prediction of Glucose and Insulin Responses of Normal Subjects after Consuming Mixed Meals Varying in Energy, Protein, Fat, Carbohydrate and Glycemic Index." *Journal of Nutrition*, 126:2807-2813 (1996).
Gannon et al. "Effects of Dose of Ingested Glucose on Plasma Metabolite and Hormone Responses in Type II Diabetic Subjects," *Diabetes Care*, 12(8):544-552 (1989).

(Continued)

*Primary Examiner* — Anna Skibinsky
(74) *Attorney, Agent, or Firm* — Hoffmann & Baron LLP

(57) ABSTRACT

The present invention provides a method of determining a standard comestible Equivalent Glycemic Load of a dietary comestible comprising: (a) establishing a reliable glycemic response index for a standard comestible, wherein the index correlates glycemic response with glycemic load; (b) determining the glycemic response produced by a dietary comestible, and (c) identifying the standard comestible glycemic load from the index which is correlated with the glycemic response of the dietary comestible.

20 Claims, 9 Drawing Sheets

(56) References Cited

OTHER PUBLICATIONS

Wolever et al. "Source and Amount of Carbohydrate Affect Postprandial Glucose and Insulin in Normal Subjects," *Journal of Nutrition*, 126:2798-2806 (1996).

Pi-Snuyer, F. Xavier, "Glycemic index and disease," *American Journal Clin. Nutrition*, 76:290S-8S (2002).

Holt et al. "Particle size, satiety and the glycaemic response," *European Journal of Clinical Nutrition*, 48:496-502 (1994).

Wolever et al. "Beneficial Effect of Low-Glycemic Index Diet in Overweight NIDDM Subjects," *Diabetes Care*, 15(4):562-565 (1992).

Holt et al., "A Satiety Index of Common Foods," *European Journal of Clinical Nutrition*, 49:675-690 (1995).

John A. Monro, et al., "Concurrent management of postprandial glycaemia and nutrient intake using glycaemic glucose equivalents, food composition data and computer-assisted meal design," *Asia Pacific J Clin Nutr*, 9(2): 67-73 (2000).

METHODS AND SYSTEMS FOR DETERMINING AND CONTROLLING GLYCEMIC RESPONSES

This application is a divisional application of U.S. application Ser. No. 10/229,952 filed on Aug. 28, 2002 now abandoned. The entire disclosure of the aforementioned application is incorporated herein by reference.

BACKGROUND OF THE INVENTION

The present invention relates to methods for establishing the Equivalent Glycemic Load of food products, and systems for selecting food products by consumers for the management of their intake of foods that elicit glycemic responses, primarily from digestible carbohydrates.

Carbohydrates can be defined in three ways; structurally (based on molecular structure), analytically (such as, for example, as defined by Federal labeling regulations), and physiologically (based on glycemic impact).

Carbohydrates defined structurally include compounds composed of at least one basic monosaccharide unit. Under this definition, carbohydrates may be further classified as simple carbohydrates and complex carbohydrates. Simple carbohydrates are monosaccharides and disaccharides. Complex carbohydrates are polysaccharides, or large molecules composed of straight or branched chains of monosaccharides.

For labeling purposes, the Food and Drug Administration (FDA) has declared that the total carbohydrate content of a food "shall be calculated by subtraction of the sum of the crude protein, total fat, moisture and ash from the total weight of the product." Such a measurement of carbohydrate content is not precise. For example, errors in the measurement of the food components being subtracted carry over into the determination of carbohydrate content. When measuring carbohydrate content in low-carbohydrate foods, such errors can typically be up to twenty to one hundred percent. (FAO/WHO Expert Panel on Carbohydrates. Carbohydrates in Human Nutrition/Total Carbohydrate Section; Rome, Italy (1997), http://hipocrates.univalle.edu.co/estudi/carbohyd.htm.) Additionally, since only the enumerated food components are subtracted, the FDA definition of carbohydrates includes components such as, lignin, gums, pectin and other fibers; as well as waxes, tannins, some Maillard products, flavonoids, organic acids, and polyols. Accordingly, the FDA definition of carbohydrates can include components which are not structural carbohydrates.

Carbohydrates defined physiologically are structural carbohydrates which elicit an immediate and significant impact on blood glucose and plasma insulin. Such carbohydrates are termed "glycemic carbohydrates," "digestible carbohydrates" or "available carbohydrates." Structural carbohydrates which do not elicit a significant impact on blood glucose and insulin are termed "non-glycemic carbohydrates."

The Food and Drug Administration (FDA) nutritional labeling requirements do not distinguish between glycemic carbohydrates and non-glycemic carbohydrates. For example, the FDA definition lumps together sugars and starches which have an immediate and significant impact on blood glucose, with fiber which does not impact blood glucose, as well as polyols, which have little, if any, impact on blood glucose.

Glycemic carbohydrates include simple carbohydrates, and some complex carbohydrates. After consumption, simple carbohydrates are rapidly absorbed, while some complex carbohydrates are typically broken down into simple carbohydrates and then absorbed. After absorption, these simple carbohydrates can elicit a rise in blood glucose levels. Non-glycemic complex carbohydrates, and some of the compounds labeled as carbohydrates on "nutritional facts" panels under the FDA definition, are not broken down into simple carbohydrates or significantly absorbed in the small intestine, but pass into the colon where they may be fermented by bacteria, or pass through the gut intact. Molecules that are not absorbed in the small intestine do not produce a rise in blood glucose levels.

The rise in blood glucose levels immediately following absorption of glycemic carbohydrates is termed the "glycemic response." Blood glucose is used immediately to provide energy, or is stored in the form of glycogen in the liver and muscles to be utilized when required by the body's energy demands. The transport of glucose from the blood into storage in liver and muscle cells is aided by the secretion of pancreatic insulin into the bloodstream. Any excess glucose, i.e. glucose which is not used as a source of energy or stored as glycogen, is converted to fat.

The normal blood glucose concentration in a healthy person after a four to eight hour fast is typically in a range of between 70 and 115 mg/100 ml of blood (Whitney and Rolfes 1993). During the first hour or so following a meal containing glycemic carbohydrates, blood glucose concentrations typically increase to 120 to 200 mg/100 ml. The secretion of insulin returns the glucose concentration to a baseline or controlled level usually within two hours after the last consumption of carbohydrates.

In individuals with diabetes mellitus, the body's mechanism for the control of blood glucose levels is defective. Either insulin production by the pancreas is diminished, or the ability of the body to use insulin is decreased. Without sufficient insulin, or without the ability of the insulin to move glucose into the cells, the consumption of glycemic carbohydrates, and subsequent absorption of glucose, results in glucose remaining in the blood for longer than normal.

The blood glucose levels of diabetics are highly sensitive to even small amounts of ingested carbohydrates or injected insulin. Such sensitivity can result in life threatening consequences. Blood glucose concentrations can rise to hyperglycemic levels in response to a meal. Diabetic coma may result. The blood glucose levels in diabetics can be regulated with the injection of insulin. However, too much insulin causes hypoglycemia which can result in insulin shock. Thus, a precise control of blood glucose levels within a narrow range is critical for diabetics. (National Institute of Health (NIH) News Release. Benefits of Tight Blood Sugar Control Endure for Years; February 9 (2000) (http://www.nih.gov/news/pr/feb2000/niddk-09.htm.)

The long term effects of diabetes also may result in severe consequences. These consequences may include heart disease, strokes, loss of vision due to retinal degeneration, loss of nerve and/or kidney function, and increased susceptibility to infection. Recent studies have shown that these long term effects of diabetes can be greatly reduced by keeping blood glucose levels under tight control.

Other metabolic disorders may be related to, or caused by, persistently high levels of blood glucose. Examples of such disorders include: insulin resistance; hyperinsulinism, which can lead to type II diabetes; hypoglycemia; hyperlipidemia; hypertriglyceridemia; and obesity.

The control of blood glucose levels in individuals without metabolic disorders is also highly desirable. For example, recent studies have shown that even transiently high blood glucose levels can lead to disease. For example, glucose molecules can attach to amino groups in tissue proteins and cross-link them into stiff yellow-brown compounds known as advanced glycation endproducts (AGEs). AGEs can form on the surfaces of long-lived proteins, such as collagen and elastin; in blood vessels and heart muscle; and in the crystallin of the lens. AGEs may destroy normal protein structure, inhibit protein physiological function and cause damage that leads to irreversible disease conditions in vital organs. (Vlassara H; Bucala R; Striker L; Pathogenic Effects of Advanced Glycosylation: Biochemical, Biologic and Clinical Implications for Diabetes and Aging. *Lab. Invest.* 70(2): 138-51 (February 1994).)

The rate of AGEs accumulation and the degree of stiffness they produce are proportional to blood glucose levels, and the length of time high levels persist.

Additionally, controlling blood glucose levels can be critical in achieving weight loss. (Ranjana Sinha et al. Prevalence of Impaired Glucose Tolerance among Children and Adolescents with Marked Obesity. *New Eng J. Med* 346(11):802-10 (March 2002).) For example, effective weight reduction can be achieved with a diet which minimizes blood glucose levels to the point of inducing ketosis in the body, where fat instead of carbohydrates serves as a primary fuel source. (Robert C. Atkins, MD, *Dr. Atkins' New Diet Revolution* (2002)).

Also, it is beneficial for athletes to control their blood glucose levels in order to enhance athletic performance. Depending on whether an athletic activity requires prolonged endurance or a brief expenditure of energy, adjusting dietary intake of glycemic carbohydrates to control blood glucose levels to suit the particular activity can benefit performance.

Accordingly, controlling blood glucose levels has many beneficial effects, most significantly including the maintenance of good health.

A system by which to rank carbohydrate-containing foods by their ability to raise blood glucose levels has been provided (Wolever et al., *Journal of the American College of Nutrition* 8(3):235-247 (1989)). The system provides the concept of "glycemic index" (GI).

GI is defined as the glycemic response elicited by a food containing twenty-five or fifty grams of glycemic carbohydrate expressed as a percentage of the glycemic response elicited by twenty-five or fifty grams of a glycemic carbohydrate of a standard food, such as white bread or an oral glucose solution.

The blood glucose response produced by carbohydrate foods which are digested and absorbed rapidly is fast and high. Such foods have high GIs. Conversely, carbohydrates which are digested and/or absorbed slowly release glucose gradually into the blood stream, and have low GIs.

Factors which influence the rate of digestion include food form, particle size, chemical structure (e.g., stage of ripeness), processing (e.g., degree of cooking) and macronutrient content (i.e. fat, protein and soluble fiber content). Fat and protein influence glycemic responses by delaying upper gastrointestinal transit and increasing insulin secretion, respectively.

The GI system is not easily applied by an average individual to his daily diet for several reasons.

GI assesses the glycemic carbohydrate portion of food without taking into account the food's glycemic carbohydrate density. Thus, average serving sizes are not taken into account. For example, since carrots contain a large portion of fiber and water, in addition to glycemic carbohydrate, a fifty gram glycemic carbohydrate portion of carrots is about six or seven average servings of carrots. Whereas, only a quarter cup of sugar contains a fifty gram portion of glycemic carbohydrate. That is, measure for measure, sugar contains far more glycemic carbohydrate than carrots contain. Since the glycemic carbohydrate density of food products are not taken into account, the odd result is that carrots have a GI of 71 and sugar has a GI of 65. Thus, an individual may be misled to believe that an average serving size of carrots produces a greater rise in blood glucose levels than a quarter cup of sugar.

Additionally, GI is a number without units. Therefore, an individual is not provided with a tangible measure by which to evaluate glycemic responses when making dietary choices.

Moreover, the determination of GI presents researchers with several difficulties. GI requires a determination of the glycemic carbohydrate content of both the standard food and the test food.

Most researchers obtain such content information from food composition tables or from food manufacturers' data. However, as discussed above, due to the different ways in which carbohydrate content of food is measured, such information is not uniform. The variation in the GI values of similar foods reported by researchers reflects this lack of uniformity.

To avoid relying on composition tables and manufacturers' labels, an individual researcher may measure the glycemic carbohydrate content of the food products. However, the addition of this step is cumbersome. Also, the methods used by different researchers to assess glycemic carbohydrate content vary.

Moreover, the measurement of glycemic response which relies on a measure of the glycemic carbohydrate content in a food product is inherently an approximation. That is, actual physiological conditions of the human body which may affect such responses may not fully be taken into account.

Another system which attempts to assess the glycemic responses produced by food uses the concept of glycemic load (GL). GL is calculated by multiplying the amount of glycemic carbohydrate in a portion of a test food and the GI of the food.

Accordingly, since the calculation of GL values includes determining GI values, the shortcomings and inaccuracies originating from GI values carry over to the calculation of GL values. For example, Foster-Powell et al. determine carbohydrate content for the calculation of GI values, and thus necessarily for GL values, from food composition tables. (*Am J Clin Nutr* 76:5-56 (2002).) Also, since the glycemic carbohydrate content in the test food is required to be measured to calculate a GL value, a further approximation is included in the calculation of the GL value.

Additionally, since GL includes the measurement of GI, the glycemic responses at either twenty-five or fifty grams of glycemic carbohydrate are used in the calculation of GL. Accordingly, it has been assumed that the functional relationship between glycemic response and glycemic carbohydrate load at either of these loads would apply to lower glycemic carbohydrate loads. That is, nutritional art and technology have not determined the actual functional relationship between glycemic response and carbohydrate portions which are less than twenty-five grams.

However, the evaluation of the glycemic responses produced by foods containing small glycemic carbohydrate portions, such as less than fifty or less than twenty-five grams, is highly important for numerous applications.

For example, as described above, the ability for diabetics to precisely control their glycemic responses is critical. It may be necessary to know the glycemic response produced by a food containing a glycemic carbohydrate portion of less than fifty grams in order to avoid insulin shock or diabetic coma.

Additionally, dieters, and those following a controlled carbohydrate lifestyle, typically consume small portions, and thus would benefit from an evaluation of glycemic responses produced by small food portions. Without such information about small portions, a dieter may choose foods which produce high glycemic responses thereby stimulating appetite.

Also, athletes typically consume small portions before engaging in athletic activities, or may consume food while performing an activity. Thus, it would be beneficial to have a method by which to assess glycemic responses of foods containing small glycemic carbohydrate portions to enhance athletic performance.

Accordingly, there is a need for the evaluation of the glycemic responses produced by food products which is easily implemented and understood by an average individual. Additionally, there is a need for a method by which researchers would be able to more easily and accurately evaluate food-produced glycemic responses. There is especially a need for a standard evaluation of glycemic responses produced by foods which contain less than twenty-five grams of glycemic carbohydrates.

SUMMARY OF INVENTION

The present invention has several aspects all of which include a systematic evaluation of glycemic responses elicited by the consumption of dietary comestibles. The invention includes establishing a reliable glycemic response index for a standard comestible at several glycemic loads. The index correlates glycemic response with glycemic load. The loads can be expressed in grams of glycemic carbohydrate of the standard comestible, grams of the total weight of the standard comestible, or uniform units of the standard comestible, such as a slice of white bread. In terms of glycemic carbohydrate, preferably the loads are below fifty grams, more preferably below forty grams, and most preferably below thirty grams.

In one aspect of the invention, a method is provided by which a standard comestible Equivalent Glycemic Load (EGL) of a dietary comestible is determined. This method includes determining the glycemic response produced by the dietary comestible. The standard comestible glycemic load which is correlated with this glycemic response is identified from the index. Such load is the standard comestible EGL of the dietary comestible.

The dietary comestible used in the method can be a single food product, or more than one food product, i.e. a mixed meal. The standard comestible used in this method is preferably white bread or glucose.

An EGL, in terms of glycemic carbohydrate load of a standard comestible, can be converted into terms of the total weight of the standard comestible, or, if applicable, into terms of a uniform unit of a standard comestible. A preferred uniform unit is a slice of white bread.

The glycemic responses are preferably determined from plasma glucose levels or from capillary glucose levels. Glycemic responses are preferably calculated in terms of incremental area under a glycemic response curve (IAUC). The IAUC can be calculated by several methods, such as by evaluating only the incremental area above a baseline, the baseline being the glycemic response prior to consumption of a comestible; or by subtracting the incremental area below a baseline from the incremental area above the baseline.

In another aspect of the invention, the standard comestible EGL is determined for, and assigned to, several dietary comestibles. The dietary comestibles are classified according to their EGL values.

Moreover, the present invention includes a method of controlling blood glucose levels in an individual. The method includes identifying, and selecting, a dietary comestible according to its EGL. A comestible which has a selected EGL is included in the diet of the individual, thereby controlling the blood glucose levels of the individual. A dietary regimen can be constructed for the individual identifying selected dietary comestibles.

Preferably, the selected EGL is low. An individual making such selection can be a diabetic, or someone who is following a low glycemic diet. An example of a dietary comestible with a low white bread EGL is a comestible which produces the same glycemic response as less than a half slice of white bread produces.

The method can further include substituting a comestible with a low EGL for a comestible, presently in the diet of the individual, which has a high EGL.

In yet a further aspect of the invention, a method of delivering a comestible which produces a low glycemic response in an individual, by identifying a comestible according to its EGL, is provided. A comestible with a low EGL is selected for consumption, so that a comestible consumer delivers to him/herself a comestible which produces a low glycemic response.

In an additional aspect, the invention provides a method of controlling glycemic comestible consumption of an individual at a desired level. Dietary comestibles are identified according to EGL. A dietary comestible is selected which contains an EGL which is within a desired level. A desired level is evaluated in terms of amount of EGL to be consumed during a selected duration. The selected comestible is consumed.

Preferably, a desired level is a low level of glycemic comestible consumption. An example of a desired low level is approximately equal to a daily white bread equivalent of one to two slices of white bread.

In another aspect, the invention provides a method of managing dietary intake of glycemic comestibles of an individual to produce desired blood glucose levels. Dietary comestibles are identified according to EGL. A dietary comestible is selected which produces desired blood glucose levels. The selected comestible is consumed. Desired blood glucose levels are low to normal levels, for example, from about 70 to 125 mg/100 ml of blood.

In yet a further aspect, the invention includes a system to reduce glycemic responses in an individual. The system includes a distinct comestible, and indicia associated with the comestible which reports the EGL contained in the distinct comestible.

The indicia can be associated with the distinct comestible in any way which provides a comestible consumer with a report of the EGL contained in the distinct comestible, e.g., the indicia can appear on the packaging of the distinct comestible.

An EGL can be in terms of the glycemic carbohydrate weight of the standard comestible. Preferably, an EGL value is in terms of the total weight of the standard comestible, and more preferably an EGL value is in terms of a portion size of a uniform unit. The indicia can report EGL values in numerical form or in graphical form.

The system can further include instructions for consumption of the distinct comestible to reduce glycemic responses in an individual. The instructions preferably include guidance for substituting the indicia-associated comestible for comestibles presently in the diet of the individual which have a high EGL.

The methods of evaluating food products according to the glycemic responses they produce, and of controlling blood glucose levels in an individual, as described herein, provide several advantages over currently used methods.

For example, the invention provides methods of determining glycemic response, and classifying foods by glycemic response, in a manner which is more easily conceptualized than current methods, i.e. GI. The GI assigns a number to a food based on a comparison with a standard food which contains twenty-five or fifty grams of glycemic carbohydrate. Such an evaluation is difficult to envision especially since GI is without units.

In contrast, the invention assesses the glycemic response produced by a dietary food product in terms of standard food equivalent glycemic loads, such as white bread glycemic equivalents. That is, the invention quantifies glycemic response in terms of a standard food dose. Moreover, unlike GI, the standard food equivalent glycemic loads provided by this invention evaluates the glycemic response produced by actual serving sizes. In this way, an individual is provided with an easily implemented method by which to guide his dietary choices.

Furthermore, unlike GI and GL, the invention does not require the determination of the glycemic carbohydrate content of foods. Thus, the invention avoids the inaccuracies and complications that come from such determinations.

As another benefit, the methods of the invention provide a systematic direct evaluation of glycemic responses produced by food products containing glycemic loads of below twenty-five grams, in particular food products containing glycemic carbohydrate loads of below twenty-five grams. Thus, the invention allows individuals to narrowly control their glycemic responses.

And, the present invention provides a functional relationship between glycemic response and glycemic carbohydrate loads of below twenty-five grams. Before this invention, such a functional relationship was not adequately defined.

As another advantage, the present invention provides a system to reduce blood glucose levels in an individual. This system includes a food product associated with indicia reporting glycemic response in terms of standard food equivalent glycemic loads. Such a system greatly benefits individuals with metabolic disorders and dieters. Before this invention, food products associated with such information were not available.

For a better understanding of the present invention, reference is made to the following description, taken in conjunction with the accompanying drawings, and the scope of the invention set forth in the claims.

DETAILED DESCRIPTION OF THE INVENTION

The methods of the invention provide a systematic evaluation of glycemic responses elicited by the consumption of dietary comestibles. The invention also includes methods and systems for controlling blood glucose levels in a human being, and for managing the consumption of glycemic comestibles, particularly those comestibles containing glycemic carbohydrates. Conceptually simple methods to assess the glycemic responses elicited by dietary comestibles are provided.

A glycemic response elicited by the consumption of a dietary comestible is evaluated in comparison with the glycemic response elicited by the consumption of a standard comestible. A glycemic response is the rise in blood glucose concentration in an individual following the consumption and absorption of a glycemic comestible. A glycemic comestible is a comestible which elicits a glycemic response. Typically, a glycemic response of a comestible is primarily elicited by the glycemic carbohydrate content of the comestible.

A glycemic response is quantified by measuring the degree and duration that blood glucose concentration is elevated in an individual in response to the consumption of a particular comestible being tested at a particular load. This elevation can be plotted with the time of measurement on the horizontal axis and the blood glucose concentration on the vertical axis. Such a plot is termed a blood glucose response curve. Blood glucose concentrations are typically expressed as milligrams per 100 milliliters of blood, or millimoles per liter of blood.

The blood glucose concentration measured prior to consumption of the comestible is typically shown at time zero on blood glucose response curves. This concentration is referred to as the concentration at baseline. In response to the consumption of a comestible, the blood glucose concentration typically increases to a peak value and then returns to the baseline after a couple of hours.

Figure 1:
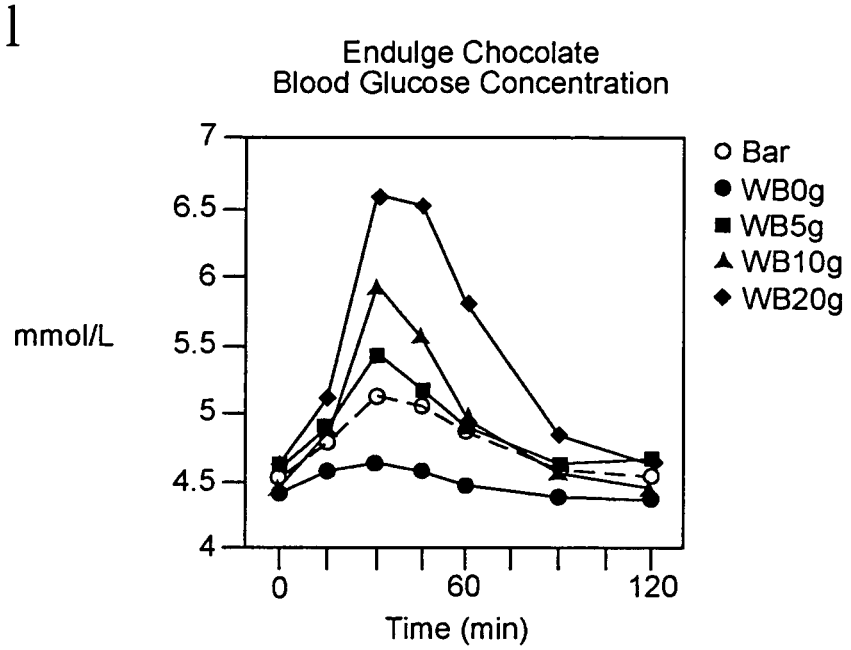
FIG. 1 shows blood glucose response curves for Atkins' Endulge Chocolate bar, and white bread at glycemic carbohydrate loads of zero, five, ten and twenty grams.
Figure 2:
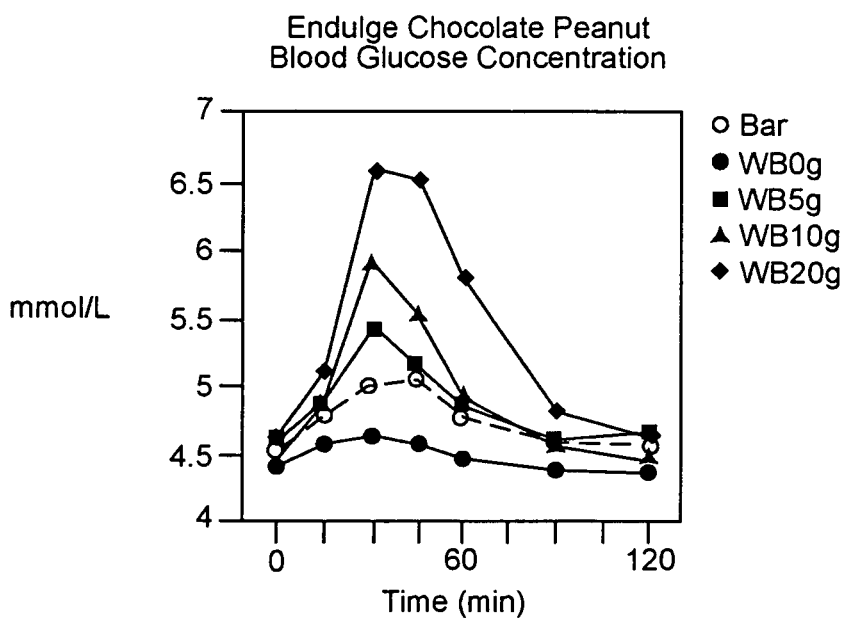
FIG. 2 shows blood glucose response curves for Atkins' Endulge Chocolate Peanut bar, and white bread at glycemic carbohydrate loads of zero, five, ten and twenty grams.
Figure 3:
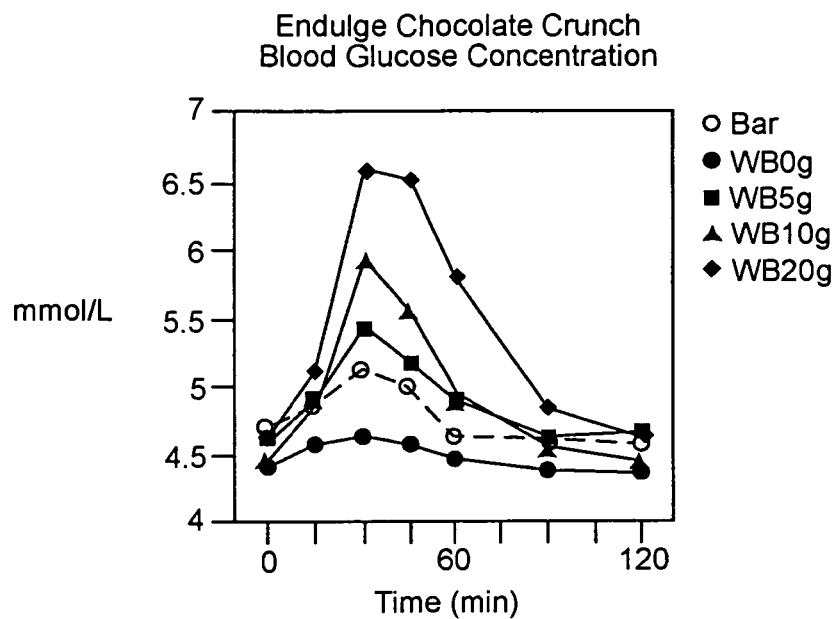
FIG. 3 shows blood glucose response curves for Atkins' Endulge Chocolate Crunch bar, and white bread at glycemic carbohydrate loads of zero, five, ten and twenty grams.

Examples of blood glucose response curves are shown in FIG. 1 for five different loads of the same comestible. As can be seen from the figure, each of these loads defines a different curve.

The glycemic response associated with a particular comestible at a particular load can be expressed by a single numerical value. For example, the incremental area under a blood glucose response curve defined by the particular comestible can be calculated. This area can be referred to as the IAUC associated with the particular comestible at the particular load.

The invention includes establishing a reliable glycemic response index for a standard comestible. The index is a correlation of different glycemic loads of a standard comestible with the glycemic responses produced by such loads. A glycemic load is the amount, dose or portion of the standard comestible which contributes to the glycemic response elicited by the standard comestible. The glycemic load can be expressed in grams of glycemic carbohydrate of the standard comestible, in grams of the total weight of the standard comestible, or in uniform units of the standard comestible, such as a slice of white bread.

The index is used to evaluate the glycemic response elicited by dietary comestibles in comparison with the glycemic response elicited by a standard comestible.

A dietary comestible, for the purposes of this specification, is any substance which is ingestible or edible. Dietary comestibles include foods from all of the basic food groups, and foods composed of any nutrient type, including, for example, proteins, fats, and carbohydrates. Dietary comestibles can be natural food products, e.g., fruits and vegetables; or manufactured and processed food products, e.g., bakery goods, confectionaries, breakfast cereals, processed meats, pasta, etc. Further examples of dietary comestibles include sports bars, snack foods, convenience foods, meal replacement products, nutritional supplements, functional foods, medical foods, enteral/parenteral solutions and pharmaceutical products. Dietary comestibles can be in any form including, for example, solid, semi-solid and liquid. Examples of dietary comestible forms include gels, beverages, frozen foods, snack bars, food components and food ingredients, i.e. sweeteners. For the purposes of this specification, a dietary comestible can be a mixed meal. A mixed meal is a composite of more than one distinct food type and/or form. For example, a mixed meal can include a multi-course meal, such as a pre-packaged frozen meal.

A standard comestible, such as a dietary comestible, is any substance which is ingestible or edible. Examples of a standard comestible include all the dietary comestibles enumerated above, for example, breads, fruits, table sugar, potato, rice, breakfast cereals, etc. Since many factors can alter the chemical composition of a comestible, and thus the glycemic response produced by a comestible (such as stage of ripeness, degree of cooking, type of processing, etc.), uniformly manufactured comestibles are preferred as standard comestibles. Examples of preferred standard comestibles are manufactured foods, such as a particular type of bread, for example, white bread and rye bread; an oral sugar solution, for example, a glucose, sucrose and/or fructose solution; a nutritional bar; and instant potatoes.

In the embodiment in which glycemic load is expressed in grams of glycemic carbohydrate contained in the standard comestible, a standard comestible with a readily quantifiable glycemic carbohydrate load is preferred. An example is a standard comestible in which the total weight of the comestible is virtually equal to the glycemic carbohydrate weight of the standard comestible. Specific examples of such standard comestibles are glucose, sucrose and fructose solutions.

The index is established by measuring the glycemic responses in at least one test subject after the consumption of a standard comestible at more than one glycemic load, preferably at more than two loads. Preferably, the glycemic response is expressed as IAUC; and the loads are expressed in grams, or in uniform units of the standard comestible, such as a portion of a slice of white bread.

Preferably, the number of test subjects evaluated is from about two to about five hundred; more preferably, from about five to about one hundred; most preferably from about ten to about fifty; and optimally from about twenty to about thirty.

The index can evaluate the glycemic response produced by a standard comestible at any glycemic load. For example, glycemic loads can be evaluated for loads below two hundred grams, preferably below fifty grams, more preferably below forty grams, most preferably below thirty grams, and optimally below twenty-five grams. The loads can be evaluated at any incremental value. For example, the index can evaluate loads at one gram increments, more preferably at five and ten gram increments. As another example, glycemic loads can be evaluated for loads below eight slices of white bread, more preferably below four slices of white bread, most preferably below three slices of white bread, and optimally below two slices of white bread. The loads can be evaluated at any incremental value. For example, the index can evaluate loads in one third slice increments.

In one embodiment, the index includes glycemic response data only of test subjects who are healthy, i.e. the subjects do not have any known metabolic disorder. In another embodiment, the index includes glycemic response data only of test subjects who are known to have a particular metabolic disorder, such as mellitus diabetes type I or type II.

The index can be in any form which correlates the glycemic load of a standard comestible with its corresponding glycemic response. For example, the index can be in the form of a listing or a graph.

It has unexpectedly been discovered that below glycemic carbohydrate loads of fifty grams, the functional relationship between glycemic carbohydrate load and IAUC is linear with a strong correlation coefficient (r). A strong correlation coefficient, as defined herein, is greater than 0.975. That is, the relationship is highly amenable to a simple linear regression analysis. Relatedly, the coefficient of determination ($r^2$) was found to be unexpectedly high. A high coefficient of determination, as defined herein, is greater than 0.95. Such a value shows that over 95% of the variation of the glycemic response is explained by the variation in the glycemic carbohydrate load. Accordingly, it has been unexpectedly discovered that the glycemic response is sensitive to small loads of glycemic carbohydrates.

Accordingly, for glycemic carbohydrate loads of below fifty grams, the index can also be expressed as a linear equation, and/or the plot of a linear equation. In particular, the relationship between glycemic carbohydrate load below fifty grams and IAUC can be defined by the following linear equation:

$$IAUC = m(\text{glycemic carbohydrate load}) + b,$$

where m is a constant, b is the glycemic response at the baseline, and the load is below fifty grams.

The linear relationship implies that with each incremental increase in the load, the value of IAUC increases by the constant value, m. Thus, the equation allows the calculation of the extent to which one gram of glycemic carbohydrate of a standard comestible would raise blood glucose levels.

The equation can be plotted. For example, the loads can be plotted on the horizontal axis; and the IAUC produced by each load can be plotted on the vertical axis. Preferably, the functions are plotted so that the load values increase from left to right.

Figure 7:
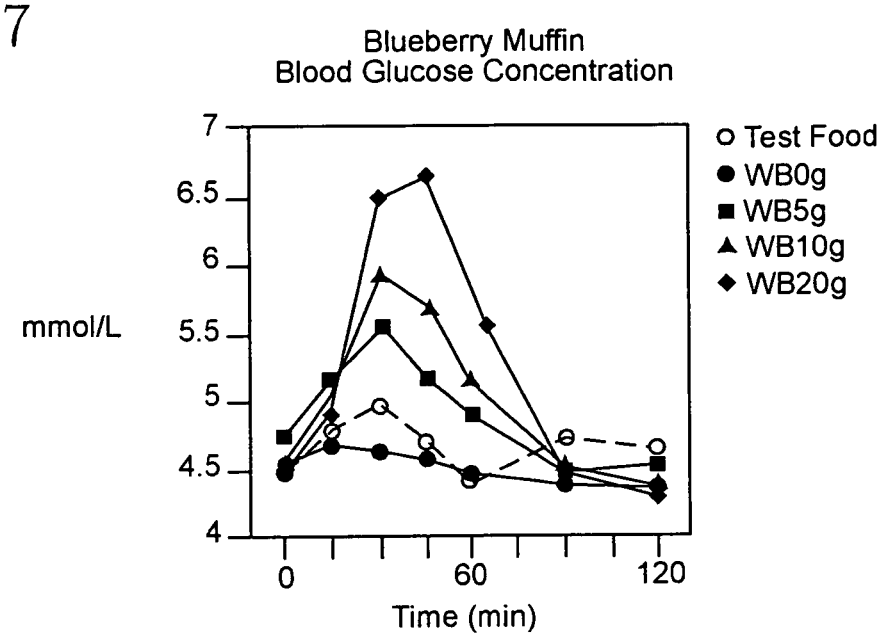
FIG. 7 shows blood glucose response curves for Atkins' Blueberry Muffin, and white bread at glycemic carbohydrate loads of zero, five, ten and twenty grams.

Different standard comestibles typically provide different indices. FIG. 7 shows an example of a glycemic response index for white bread at loads of below twenty grams of glycemic carbohydrate. This index is defined by the following equation: IAUC=4.70 (glycemic carbohydrate load)+13.8.

Given observed IAUC values at a minimum of two loads, the linear relationship allows for the deduction of IAUC values at unobserved loads below fifty grams. The values can be deduced from the equation directly, or via extrapolation or interpolation.

In one embodiment of the invention, methods are provided for determining an Equivalent Glycemic Load (EGL) of a dietary comestible. The method includes establishing a reliable glycemic response index for a standard comestible.

In this embodiment, the glycemic response elicited by the consumption of a certain dose of a particular dietary comestible is measured. This response is located on the index. The index correlates this response with a standard comestible glycemic load. This load is identified from the index, and is the Equivalent Glycemic Load (EGL) of the particular dietary comestible for the particular standard comestible. Thus, the glycemic response elicited by a dietary comestible is provided in terms of a standard comestible glycemic load, i.e. a standard comestible EGL.

Figure 4:
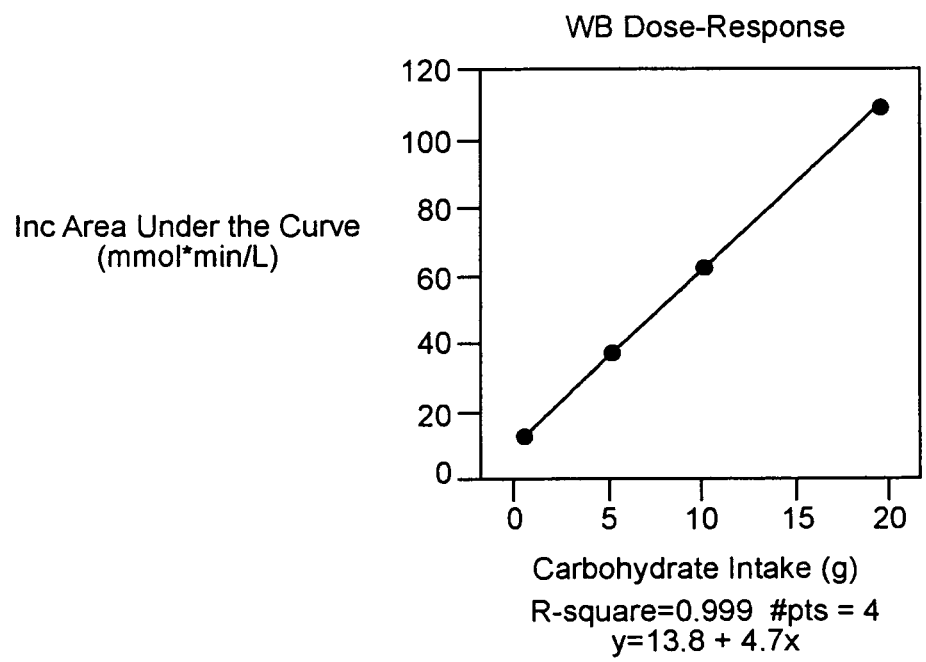
FIG. 4 shows a glycemic response index for white bread loads of below twenty grams of glycemic carbohydrate.
Figure 5:
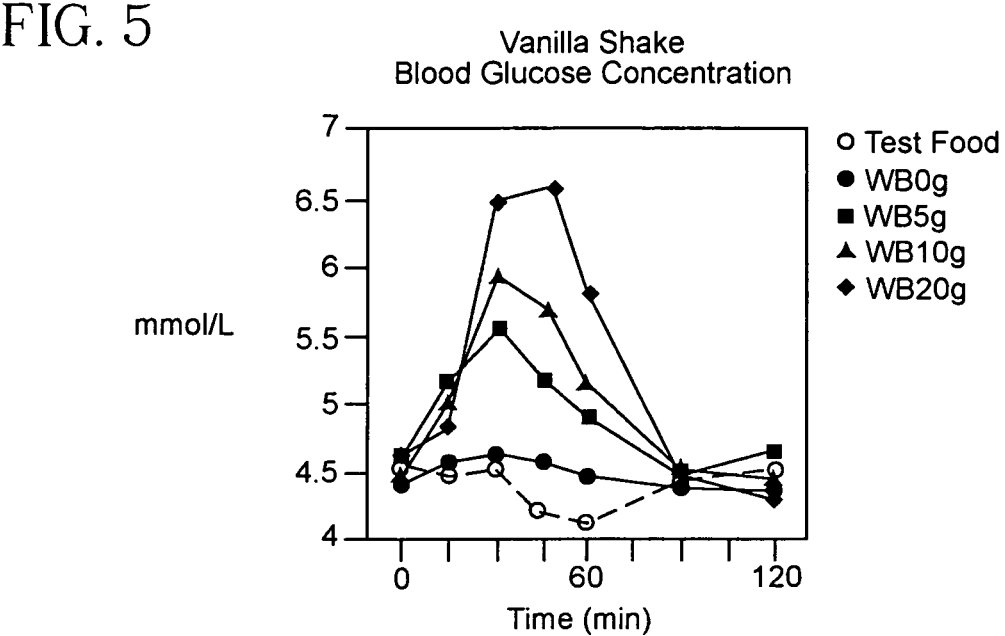
FIG. 5 shows blood glucose response curves for Atkins' Vanilla Shake, and white bread at glycemic carbohydrate loads of zero, five, ten and twenty grams.
Figure 6:
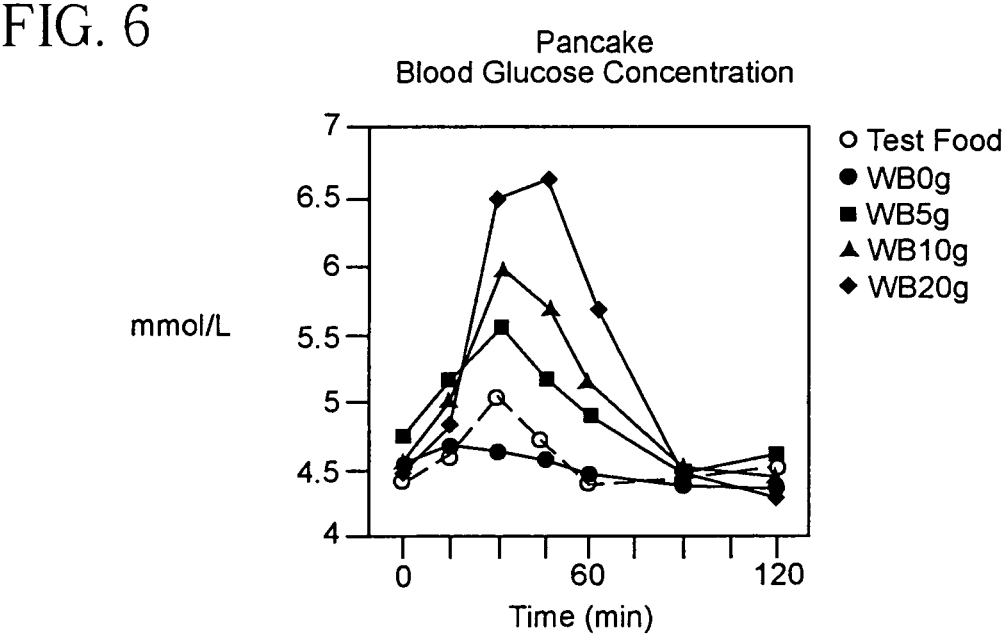
FIG. 6 shows blood glucose response curves for Atkins' Pancake, and white bread at glycemic carbohydrate loads of zero, five, ten and twenty grams.

Identification of the EGL load from the index can include locating the load from a list which correlates responses with the glycemic loads. Alternatively, if the response elicited by the dietary comestible is below the response elicited by fifty glycemic carbohydrate grams of the standard comestible, identification of the EGL can include the use of the linear equation shown above. If the standard comestible is white bread, the load can be located on a glycemic response index, such as shown in FIG. 4.

A demonstration of one of the embodiments of the methods of the present invention is shown in the Examples. In these examples, the index expresses glycemic load in terms of glycemic carbohydrate contained in a standard comestible. The glycemic response of an Atkins' Endulge Chocolate bar was found to be 32.7 mmol×min/L in terms of IAUC. Using the index shown in FIG. 4, this glycemic response is located on the index. This glycemic response is correlated with a load of about 3.3 grams of white bread glycemic carbohydrate. Thus, the white bread EGL of the bar is 3.3 grams. That is, white bread which contains 3.3 grams of glycemic carbohydrate elicits the same glycemic response as the Atkins' Endulge Chocolate bar.

EGL can be in terms of a glycemic carbohydrate load of a standard comestible, such as about 3.3 grams of white bread glycemic carbohydrate for the bar. Preferably, the EGL is in terms of the total weight of a standard comestible.

The total weight of a comestible typically includes, in addition to its glycemic carbohydrate load, the weight of, for example, water, other nutrient types and non-glycemic carbohydrates. Accordingly, the glycemic carbohydrate load of a standard comestible is not typically equal to the total weight of the standard comestible. That is, one gram of a standard comestible does not typically contain one gram of glycemic carbohydrate.

As discussed above, the index can be constructed so that the standard comestible is in terms of the total weight of, or a uniform unit of, the standard comestible. Alternatively, if the standard comestible is in terms of the glycemic carbohydrate portion of the standard comestible, it can be converted to the total weight of, or a uniform unit of, the standard comestible.

To convert an EGL which is in terms of the glycemic carbohydrate load to be in terms of the total weight, the EGL in terms of glycemic carbohydrate load is multiplied by the weight of the standard comestible which contains one gram of glycemic carbohydrate. Thus, the actual amount of a standard comestible which contains the glycemic carbohydrate load is provided. Accordingly, an individual is provided with a tangible serving size of a familiar comestible by which to evaluate the glycemic response elicited by a dietary comestible of his choice.

For example, one gram of white bread typically contains approximately half a gram of glycemic carbohydrate. Thus, if a particular dietary comestible elicits the glycemic response of four glycemic carbohydrate grams of white bread, the four grams is multiplied by two to get the glycemic response in terms of the total weight of white bread. Accordingly, eight total grams of white bread produces the same glycemic response as the particular dietary comestible. Thus, it is important to note whether the standard comestible EGL is expressed in terms of glycemic carbohydrate weight of the standard comestible, or in terms of the total weight of the standard comestible.

If the standard comestible is available in a uniform unit, then the EGL is preferably provided in a portion size of the unit. Examples of a uniform unit are a slice of any type of bread, a piece of a particular candy or food bar, or a particular cookie.

To convert a standard comestible EGL which is in terms of the glycemic carbohydrate dose to be in terms of a uniform unit, the total weight of a unit of the standard comestible, and glycemic carbohydrate dose contained in the unit, are determined. For example, a slice of white bread may weigh approximately twenty-four grams and may contain approximately twelve grams of glycemic carbohydrate. Using this information, the glycemic response elicited by a dietary comestible can be expressed as being equivalent to the glycemic response elicited by a certain unit portion of a standard comestible, e.g., a certain slice amount of white bread.

For example, the glycemic response elicited by a particular pastry can be expressed as being equivalent to the glycemic response elicited by ten slices of white bread. Or, the glycemic response elicited by an Atkins' Endulge Chocolate Crunch bar (Atkins Nutritionals, Inc.) can be expressed as being equivalent to the glycemic response elicited by approximately three tenths of a slice of white bread. Thus, the white bread EGL is three tenths of a slice of white bread. Accordingly, the glycemic response elicited by a dietary comestible is provided in an easily conceptualized manner.

The EGL can be calculated for any dietary comestible at any glycemic load, e.g., a two hundred gram load. In the embodiment in which EGL is in terms of glycemic carbohydrate load, preferably the dietary comestible elicits a glycemic response which is below the glycemic response elicited by the standard comestible at a glycemic carbohydrate load of approximately fifty grams, more preferably at a load below forty grams, most preferably at a load below thirty grams, and optimally at a load below twenty-five grams.

In another aspect of the invention, a method of classifying dietary comestibles according to their EGL value, with reference to a particular standard comestible, is provided. Preferably, the EGL is in terms of the total weight of a standard comestible, and more preferably the EGL is in terms of a portion size of a uniform unit of a standard comestible.

Classifying includes determining and assigning a standard comestible EGL value to several dietary comestibles at various serving sizes. The dietary comestibles can contain any glycemic load.

A serving size of a dietary comestible can be in terms of the weight of the dietary comestible, i.e. grams; or in terms of a standard portion, e.g. a tablespoon, a uniform unit of prepackaged brand name food, a standard size doughnut, a standard size slice of pizza, etc.

Preferably, EGL values are determined for at least ten, more preferably at least fifty, most preferably at least one hundred, and optimally at least five hundred commonly consumed dietary comestibles. EGL values were empirically derived from data obtained from nutritional studies conducted by Atkins Nutritionals, Inc.

Since metabolic disorders may affect an individual's glycemic response to dietary comestibles, preferably, more than one classification is provided. For example, a classification can be provided for healthy individuals, i.e. individuals who do not have any known metabolic disorder. Another classification can be provided for individuals who have known metabolic disorders. Alternatively, an adjustment factor can be applied to EGL values for healthy individuals to convert them to values that more accurately reflect glycemic responses of individuals with known metabolic disorders.

Classifications provided by the methods of this invention enable a comestible consumer to evaluate a dietary comestible in terms of its ability to raise blood glucose levels. A classification can be used to evaluate which dietary comestible of a set of dietary comestibles will elicit the greatest glycemic response. Thus, the effect of a dietary change on blood glucose levels can be predicted. For example, an individual is enabled to exchange a dietary comestible with a relatively high EGL value for more than one dietary comestible with low EGL values.

A EGL classification can be embodied in paper or computer readable form. For example, a EGL value can be provided on lists, menus, food packaging or in a software package.

In a further aspect of the invention, a method of controlling the blood glucose levels of an individual is provided. A dietary comestible is selected according to its standard comestible EGL value. An individual can identify the dietary comestible with the selected value by, for example, referring to a classification, as described above. Alternatively, the individual can rely on a medical practitioner's guidance. Such guidance can include determining the individual's own personal glycemic responses to a series of comestibles, according to the invention.

A control can be an increase, a decrease, or maintenance of blood glucose levels in an individual. A dietary comestible with a high EGL value is selected to increase blood glucose levels; a dietary comestible with a low EGL value is selected to decrease and/or maintain blood glucose levels. A dietary comestible which has the selected EGL is included in the dietary regimen of the individual.

Preferably, dietary comestibles which have the selected EGL are substituted for comestibles presently in the diet of the individual. A dietary regimen can be constructed for an individual in which such substitutions are set forth. These substitutions can be provided in a paper or computer readable format.

A control of blood glucose levels of the individual can be for a short duration or for a long duration. If the blood glucose levels of the individual are to be controlled for a short duration, for example, for an hour to a week, the selected comestible is made part of the individual's diet for the duration. If the blood glucose levels of the individual are to be controlled for a long duration, for example, from six months to an indefinite period of time, the selected comestible is included in the daily diet of the individual for such duration.

An example of an individual who would select a comestible that produces high blood glucose levels for a short duration is an athlete performing a short duration exercise. High blood glucose levels may provide extra energy for the exercise.

An example of an individual who would select comestibles that produce low blood glucose levels is an individual with a metabolic disorder. Examples of metabolic disorders include diabetes, insulin resistance, hyperinsulinism, hypoglycemia, hyperlipidemia, hypertriglyceridemia and obesity. As described above, an individual with a metabolic disorder, for example a diabetic, can greatly benefit from selecting dietary comestibles which keep blood glucose levels in a narrow normal range.

Another example of an individual who would select comestibles that produce low blood glucose levels is an individual following a low glycemic diet, i.e. low glycemic carbohydrate diet. An example of a low glycemic carbohydrate diet is set forth in *Dr. Atkins New Diet Revolution* (Harper Collins Publishers, Inc. 2002).

Studies have shown that persistently high blood glucose levels can be associated with the following diseases and/or disorders: metabolic disorders; cardiovascular disease; certain cancers, e.g., colon and breast cancer; high blood HDL-cholesterol concentration; and/or AGES. (Foster-Powell et al. *Am J Clin Nutr* 76:5-56 (2002).) Accordingly, selecting comestibles that produce low blood glucose levels may reduce the risk of acquiring, or may prevent acquiring, the aforementioned diseases and/or disorders.

Since a EGL value assigned to a particular comestible is evaluated in reference to a particular standard comestible, the standard comestible used in the evaluation should be considered when determining if a EGL value is low or high.

For example, a selected dietary comestible with a low white bread EGL, in terms of slice of white bread, is about 0.5 slice. That is, in this case, the selected dietary comestible produces the same glycemic response as half a slice of white bread. Depending upon the degree to which an individual would like to maintain and/or decrease his blood glucose levels, a low white bread EGL of a dietary comestible can be, for example, less than 0.85 of a slice, more preferably less than 0.65, most preferably less than 0.4, and optimally less than 0.1.

A selected dietary comestible with a high white bread EGL, in terms of slice of white bread, is about 1.5 slice. That is, in this case, the selected dietary comestible produces the same glycemic response as one and a half slices of white bread. Depending upon the degree to which an individual would like to increase his blood glucose levels, a high white bread EGL of a dietary comestible can be, for example, over one slice, more preferably over two slices, most preferably over three slices, and optimally over four slices.

In a further aspect of the invention, a method of delivering a dietary comestible which produces a low glycemic response in an individual is provided. A dietary comestible with a low EGL is selected for consumption. The individual can select the comestible by referring to a classification, as described above. Alternatively, the individual can rely on guidance from a medical practitioner, diet plan organizer, or food packagers. The individual consumes the selected dietary comestible.

In another aspect of this invention, a method for controlling glycemic comestible consumption, primarily glycemic carbohydrate consumption, of an individual at a desired level is provided. Dietary comestibles are identified according to their EGL values. An individual can identify comestibles according to their EGL values by, for example, referring to a classification, as described above. Alternatively, the individual can rely on guidance from a medical practitioner or diet organizer.

A desired level of consumption is evaluated in terms of amount of EGL consumed during a predetermined duration. Control of glycemic comestible consumption of an individual at a desired level can include limiting the consumption of EGL to a maximum level over a predetermined period of time.

For example, the consumption of glycemic comestibles can be limited to a desired maximum daily level. In such case, the total amount of glycemic comestibles, in terms of EGL, to be consumed for the day is selected. This total daily amount can be chosen by the individual, or prescribed by a medical practitioner or diet plan organizer. A running total of EGL values assigned to the comestibles consumed by an individual in the course of a day is recorded. Once the individual reaches the maximum daily level of EGL, no more glycemic dietary comestibles are consumed by the individual that same day.

An example of a desired daily level of glycemic comestible consumption in an individual following a low glycemic comestible diet is approximately equal to a daily white bread EGL, in terms of glycemic carbohydrate weight, of five to forty grams, more preferably from approximately ten grams to thirty grams, most preferably from approximately ten to twenty-five grams, and optimally from approximately ten to twenty grams.

The daily total EGL value is preferably in terms of the total weight of a standard comestible. Since one gram of white bread typically contains approximately half a gram of glycemic carbohydrate, the aforementioned daily values can be multiplied by two to obtain the daily total EGL in terms of total weight of white bread.

The daily total EGL value is more preferably in terms of a portion of a uniform unit of a standard comestible. For example, a slice of white bread may contain approximately twelve grams of glycemic carbohydrate. Thus, in this case, approximately 1.7 slices of the white bread is equal to twenty grams of glycemic carbohydrate. Accordingly, an individual following a low glycemic carbohydrate diet can, for example, limit his daily glycemic carbohydrate intake to an EGL of 1.7 slices of such white bread. Examples of other total daily values for individuals following a low glycemic carbohydrate diet are less than three slices of white bread, less than two slices, less than one slice and less than a half a slice.

Preferably, the control of carbohydrate consumption includes substituting comestibles with low EGL values for comestibles presently in the diet of the individual with high EGL values. A dietary regimen can be constructed for an individual in which such substitutions are set forth. These substitutions can be provided in a paper or computer readable format.

In another aspect of the invention, a method of managing dietary intake of glycemic comestibles of an individual to produce desired blood glucose levels is provided. Dietary comestibles are identified according to their EGL values, as described above. Comestibles with high or low EGL values are selected for consumption according to whether blood glucose levels are to be increased or decreased, and the degree to which the levels are to be increased or decreased. A selected comestible is consumed by the individual.

An example of a desired low blood glucose level is in a range of between 70 and 125 mg/100 ml of blood. An example of a desired high blood glucose level is in a range of between 135 and 200 mg/100 ml of blood. A high blood glucose level is typically desired by athletes performing short duration athletic activites.

Methods by which to treat, or prevent, metabolic disorders are provided. The methods, discussed above, by which to control blood glucose levels; control glycemic comestible consumption, in particular glycemic carbohydrate consumption; and manage the dietary intake of glycemic comestibles can be used to treat, or prevent, metabolic disorders. Methods are provided by which to reduce the risk of acquiring, or prevent acquiring, the following diseases and/or disorders: metabolic disorders; cardiovascular disease; certain cancers, e.g., colon and breast cancer; high blood HDL-cholesterol concentration; and/or AGES. The methods, discussed above, by which to control blood glucose levels; control glycemic comestible consumption, in particular glycemic carbohydrate consumption; and manage the dietary intake of glycemic comestibles can be used to reduce the risk of acquiring, or prevent acquiring, the above enumerated diseases and/or disorders In one embodiment of the invention, the determination of EGL values for comestibles can be used to provide a system to reduce blood glucose levels in an individual. The system includes a distinct comestible which produces a low glycemic response; and indicia associated with the distinct comestible which reports the EGL contained in the distinct comestible. Preferably, the distinct comestible produces a glycemic response which is below the glycemic response produced by a standard comestible containing approximately one hundred grams of glycemic carbohydrate, more preferably approximately fifty grams, and most preferably approximately twenty grams.

The distinct comestible can be of any form or type, as described above for dietary comestibles. For example, the distinct comestible can be a packaged food bar, a frozen mixed meal, or a food additive. Examples of distinct comestibles are Atkins' Endulge Chocolate, Endulge Chocolate Peanut and Endulge Chocolate Crunch bars (Atkins Nutritionals, Inc.).

The indicia can be associated with the distinct comestible in any way which provides a comestible consumer with a report of the EGL of the distinct comestible. For example, the indicia can appear on the packaging of the distinct comestible. If the comestible is sold in loose form, the indicia can be provided in a listing or menu. Such listing or menu can be embodied in paper or computer readable format.

Preferably, a EGL value is in terms of the total weight of the standard comestible, and more preferably a EGL value is in terms of a portion size of a uniform unit.

Indicia can report EGL values in numerical form. Alternatively, EGL values can be depicted in graphical form. For example, if a EGL is reported in terms of white bread slices, then the EGL value can be depicted as a drawing of the corresponding number of slices. Such a drawing can include fractional amounts, e.g., a drawing of one and a half slices of white bread.

Indicia can also report an EGL value in terms of a daily total amount of glycemic comestible allowed on a particular low glycemic comestible diet. For example, the EGL contained in the distinct comestible can be reported in terms of a fractional amount, or percent amount, of the daily total amount of allowed glycemic comestibles. Such fractional/percent amount can be reported in numerical form. Alternatively, this fractional amount can be reported by a graphical depiction, such as a pie chart. For example, a whole pie chart can represent the total daily amount of allowed glycemic comestibles on a particular diet. A shaded portion of the pie chart can represent the contribution to the daily total that consumption of the distinct comestible would make.

For example, if a particular low glycemic comestible diet prescribes a daily total of twenty grams of glycemic carbohydrate, then a distinct comestible which contains two grams of EGL would contain one tenth of the daily amount. Accordingly, one tenth of a pie chart associated with the distinct comestible would be shaded.

The system can further include instructions for consumption of the distinct comestible to reduce blood glucose levels in an individual. The instructions preferably include guidance for substituting the indicia-associated comestible for comestibles presently in the diet of the individual which have a relatively high EGL.

It is to be appreciated that the methods of the present invention described herein above may be performed using a general purpose computer or processing system which is capable of running application software programs, such as an IBM personal computer (PC) or suitable equivalent thereof. Preferably, the application program code is embedded in a computer readable medium, such as a floppy disk or computer compact disk (CD). Furthermore, the computer readable medium may be in the form of a hard disk or memory (e.g., random access memory or read only memory) included in the general purpose computer.

As appreciated by one skilled in the art, the computer software code may be written, using any suitable programming language, for example, C or Pascal, to configure the computer to perform the methods of the present invention. While it is preferred that a computer program be used to accomplish any of the methods of the present invention, it is similarly contemplated that the computer may be utilized to perform only a certain specific step or task in an overall method, as determined by the user.

Preferably, the methods of the present invention are used with one or more displays (e.g., conventional CRT or liquid crystal display) provided with the processing system for presenting an indication of, for example, the final result of the method. The display may preferably be utilized to present such information graphically (e.g., charts and graphs) for further clarity.

In addition to performing the necessary calculations and processing functions in accordance with the present invention, the general purpose computer may also be used, for example, to store data pertaining to empirically derived EGL values. Such information may be stored on a hard disk or other memory, either volatile or non-volatile, included in the computer. Similarly, the information may be stored on a computer readable medium, such as floppy disk or CD, which can be transported for use on another computer system, as appreciated by those skilled in the art. In this manner, the methods of the present invention may be performed on any suitable general purpose computer and are not limited to a dedicated system.

An example of performing a method of the present invention by using a general purpose computer or processing system which is capable of running application software programs follows.

The method includes storing data in a computer memory from which can be obtained an EGL value for each of a variety of dietary comestibles in several serving sizes. EGL values in reference to at least one, preferably several, standard comestibles are also stored. Preferably, EGL values in terms of glycemic carbohydrate content of a standard comestible, in terms of the total weight of a standard comestible, and in terms of a uniform unit of a standard comestible are also stored. An EGL value is obtained by the user (e.g., a comestible consumer, or a diet plan organizer) for a selected dietary comestible, at a selected serving size, in reference to a selected standard comestible. Preferably, a minimum and/or maximum daily total EGL value appropriate to produce glycemic comestible consumption at a selected daily level is obtained from the computer memory or inputted by the user. A sum of the comestible consumer's daily EGL value, including the EGL of the selected dietary comestible, is calculated. A determination is made as to whether the calculated sum lies within the determined appropriate minimum and/or maximum daily total EGL value. If the sum lies within the determined minimum and/or maximum, the individual consumes the selected dietary comestible.

General Experimental Protocols for Obtaining Glycemic Response Data

The procedures by which blood samples are obtained from test subjects, and the methods used to quantify blood glucose levels, influence the value of a glycemic response. Accordingly, when comparing the glycemic responses elicited by comestibles, it is preferable that similar procedures and methods are used to obtain and quantify the responses. In particular, when comparing the glycemic response elicited by a dietary comestible with a standard comestible, it is preferable that similar procedures and methods be used to obtain and quantify the responses.

In order to assure that the glycemic response is attributable to the comestible being tested, test subjects preferably fast for about four to fifteen hours before consuming the test comestible. Preferably, the test subjects fast for approximately similar lengths of time.

The physical characteristics of a test subject can affect the glycemic response to a particular comestible. For example, the responses of an individual test subject to a particular comestible can vary on a daily basis. This variation can be due to, for example, the fasting blood glucose value of a test subject on the day of the test. To reduce such variability, the glycemic response of a particular subject to the same comestible is preferably evaluated on more than one occasion, e.g. on three separate days. The mean of multiple responses is preferably calculated, and considered as the glycemic response of the test subject for the particular test comestible.

Additionally, different test subjects may differ in their glycemic responses to a particular comestible. Physical characteristics which may affect responses include age, sex, body fat index, and glucose tolerance status. To reduce such variability, the responses to a particular comestible are preferably determined for more than one test subject, and the mean of these responses is calculated. Such mean can be considered to be the glycemic response associated with a particular comestible. For example, the mean of the glycemic responses of three test subjects to a particular comestible can be calculated, and considered to be the glycemic response associated with the particular comestible.

The main physical characteristic that affects glycemic response is the glucose tolerance status of the test subjects. Accordingly, preferably, the glycemic responses of test subjects who have known metabolic disorders are evaluated separately from healthy subjects, i.e. subjects who do not have a known metabolic disorder.

The period of time blood glucose levels are measured also affects the value of the glycemic response associated with a particular comestible. The fasting blood glucose level of a test subject is known as the baseline measurement. Return to the baseline after consumption of a comestible is typically within two to three hours in healthy subjects, and typically within three to five hours in diabetics. Accordingly, the blood glucose level is measured within a three hour test period, preferably within a two hour test period, after consumption of a particular comestible in healthy subjects. In diabetic subjects, the blood glucose level is measured within a five hour test period, preferably within a three hour test period, after consumption of a particular comestible.

As the number of blood glucose level measurements obtained within a test period is increased, the more defined the glycemic response to a particular comestible becomes. The blood glucose levels are measured at least once during a test period, more preferably at least twice during a test period, most preferably at least four times during a test period, and optimally at least eight times during a test period. For example, in a two hour test period, blood glucose levels are preferably measured in fifteen minute intervals.

Glycemic response determination is also affected by the method used to obtain the blood samples. For example, blood glucose levels can be measured from capillary whole blood, or venous blood or plasma. Preferably, the blood glucose levels are based on measurement of capillary whole blood. The rise in blood glucose levels in response to glycemic carbohydrates is greater in capillary blood vis-à-vis venous plasma. Thus, differences between comestibles are easier to detect statistically using capillary blood glucose. Also, the results obtained from capillary blood are less variable than those obtained from venous plasma. (Jackson et al. *Metabolism* 32:706-10 (1983).) Blood glucose concentration can be analyzed by any reliable method known in the art including, for example, by a glucose oxidase method with a Beckman glucose analyzer and oxygen electrode (Fullerton, Calif.).

The incremental area under the curve (IAUC) can be calculated in several ways. Preferably, only the IAUC above the baseline is considered. The baseline is the glycemic response prior to consumption of the comestible being tested. However, the net IAUC can be calculated instead, i.e. the area below the baseline can be subtracted from the area above the baseline. A net IAUC calculation would produce a different value from the preferred IAUC calculation for a particular comestible if the glucose levels associated with the particular comestible fall below the baseline during the measurement period. Preferably, the same method for calculating IAUC is used for evaluating the glycemic responses of the standard and dietary comestibles.

In one embodiment, if more than one subject is tested, the mean of their IAUCs can be used to provide an index, as described above. For glycemic carbohydrate loads of below fifty grams, another mean calculation can be used instead. In this embodiment, the linear equation which relates load to IAUC is calculated for each test subject. The mean of the glycemic responses at baseline (b); and the mean of the constants m, are then calculated. These means are then used in a linear equation which defines an index. (See the Examples.)

In any mean calculation according to the present invention, if an individual test subject's response data is an outlier, for example greater than two standard deviation units from the mean, it can be considered unrepresentative and be discarded.

The EGL evaluation can be applied to dietary comestibles which are mixed meals. In one embodiment, the mixed meal is considered to be a dietary comestible per se. That is, the glycemic response to the mixed meal can be calculated directly by measuring the glycemic response after the meal, and comparing this response with the index. Alternatively, the EGL of a mixed meal can be obtained by calculating the weighted average of the EGL of each dietary comestible component of the mixed meal. The weighing can be based on the proportion of total meal glycemic carbohydrate contributed by each of the dietary comestibles.

General Properties of Linear Regression Analysis

Linear regression analysis is a statistical procedure for fitting the best straight line through a set of data points. The line generated by the linear regression analysis can be extrapolated beyond observed values (limited to a fifty gram load). The extrapolation defines what the expected IAUC is at a particular dose beyond the observed values of a particular blood sampling. For example, if the index does not include the observed value of the glycemic response at a zero gram load, i.e. baseline, the glycemic response at a zero gram load can be extrapolated from the other observed values of the index. Similarly, given observed IAUC values at two loads, IAUC values at loads in between the two observed values can be interpolated. Interpolation is an estimate of a function between two observed values.

The quality of fit of the line to the measured values can be described by R, the correlation coefficient. That is, r is a statistic which measures the strength of the straight-line relationship. (The formula for r is: $r=[(\Sigma xy)/((\Sigma x^2)(\Sigma y^2))^{1/2}]$.) This coefficient can vary between $-1$ and $1$. A value of $0$ indicates no correlation. The value of $1$ indicates a perfect positive correlation. That is, the value of the IAUC is predicted perfectly by knowing the value of a load. (The value of $-1$ indicates a perfect negative correlation. A negative correlation would apply if the doses were plotted in decreasing value from left to right.) As can be seen from the Examples, the correlation coefficient for load values of below fifty grams is greater than 0.95.

EXAMPLES

Example 1

The glycemic responses of 1 serving (1 bar=30 g) of Atkins' Endulge Chocolate, Endulge Chocolate Peanut and Endulge Chocolate Crunch bars were determined in 10 healthy subjects (4 male, 6 female; 39±5 years of age; body mass index 23.4±0.9 kg/m$^2$), relative to the response from white bread. Each subject was studied on 7 occasions in the morning after 10-14 h overnight fasts. On each occasion, each subject consumed a test meal. One of the test meals consisted of a standard drink alone. The standard drink did not contain glycemic carbohydrate. Three of the test meals consisted of one type of bar and the standard drink. Three of the test meals consisted of white bread containing a particular amount of glycemic carbohydrate, i.e. 5 g, 10 g or 20 g; and the standard drink. The glycemic responses of each subject were determined after each test meal.

The dose response curve for bread allowed calculation in each subject of the extent to which 1 g glycemic carbohydrate from bread raised blood glucose. This allowed calculation of: 1) the amount of bread required to be consumed to elicit the same glycemic response of each test product, i.e. white bread equivalent (WBE); and 2) the glycemic response of each bar relative to the same amount of carbohydrate from bread (relative glycemic response (RGR)). The incremental area under the glycemic response curve (IAUC) increased in a linear fashion as the amount of carbohydrate consumed from bread increased from 0 to 20 g, with the correlation coefficient (r) being >0.95 in 7 of the 10 subjects. The regression equation of mean IAUC on dose of carbohydrate (d) was:

$$IAUC=4.70d+13.8 (r=0.999)$$

The RGRs of the Endulge Chocolate, Endulge Chocolate Peanut and Endulge Chocolate Crunch bars, respectively, were 39±5, 48±9 and 31±7. The amount of glycemic carbohydrate from white bread which would raise blood glucose to the same extent as the 3 bars, respectively, was 3.3±0.8 g, 3.6±1.6 g and 2.6±0.8 g. This is equivalent to about 5-7 g of white bread or about ⅕ to 2/7 of a slice of white bread.

Methods

Subjects

Ten (10) healthy subjects (3-5 male and 3-5 female) aged 18-50 years of age with a body mass index of 20-30 kg/m². Female subjects were excluded if they reported being pregnant or intending to become pregnant during the course of the study. Subjects were not following a restrictive diet, had no history of diabetes or heart disease, and were not be taking any prescription medication other than birth control pills.

| ID | Ethnicity | Sex | Age (y) | Height (cm) | Height (in) | Weight (kg) | Weight (lb) | BMI (kg/m²) |
|---|---|---|---|---|---|---|---|---|
| 1 | African-Am | M | 35 | 173.0 | 68.1 | 87.0 | 191.4 | 29.07 |
| 27 | Asian | F | 24 | 170.2 | 67.0 | 57.5 | 126.5 | 19.85 |
| 31 | Caucasian | F | 53 | 162.0 | 63.8 | 58.2 | 128.0 | 22.18 |
| 33 | Caucasian | F | 37 | 165.0 | 65.0 | 58.0 | 127.6 | 21.30 |
| 38 | Caucasian | M | 20 | 187.5 | 73.8 | 90.6 | 199.3 | 25.77 |
| 39 | Caucasian | F | 70 | 161.3 | 63.5 | 54.8 | 120.6 | 21.06 |
| 43 | Caucasian | F | 53 | 167.6 | 66.0 | 64.8 | 142.6 | 23.07 |
| 44 | Caribbean | M | 45 | 182.9 | 72.0 | 87.5 | 192.5 | 26.16 |
| 48 | Caucasian | F | 22 | 162.6 | 64.0 | 55.5 | 122.1 | 20.99 |
| 55 | Caucasian | M | 27 | 179.5 | 70.7 | 78.7 | 173.1 | 24.43 |
| | | Mean | 38.6 | 171.2 | 67.4 | 69.3 | 152.4 | 23.39 |
| | | SEM | 5.2 | 3.0 | 1.2 | 4.7 | 10.4 | 0.92 |

Protocol

Subjects each underwent 7 treatments in randomized order on separate days, with tests for each subject occurring at approximately weekly intervals. On each test day, subjects came to Glycaemic Index Testing Laboratory (55 Queen St. East, Suite 203, in the morning after a 10-14 h overnight fast, and no ethanol consumption within 24 h. After being weighed and having a fasting blood sample obtained by finger-prick prick, the subject then consumed a test meal within 10 minutes, and further blood samples were obtained at 15, 30, 45, 60, 90 and 120 minutes after the start of the test meal. Subjects were also given a drink of their choice of 1 or 2 cups of either water, coffee or tea, with or without 60 ml of 2% milk. The drink chosen by each subject remained the same on each test day.

The treatments consisted of one serving (1 bar=30 g) of Endulge Chocolate, Endulge Chocolate Peanut and Endulge Chocolate Crunch bars, or the standard drink alone (0 g white bread), or an amount of white bread containing 5, 10 or 20 g glycemic carbohydrate. Bread was baked in a bread maker in loaves containing 50 g glycemic carbohydrate. The ingredients for each loaf (250 ml warm water, 334 g all purpose flour, 7 g sugar, 4 g salt and 6.5 g yeast) were placed into the bread maker according to instructions, and the machine turned on. After the loaf had been made, it was allowed to cool for an hour, and then weighed and after discarding the crust ends, the remainder was divided into portion sizes containing 5, 10 or 20 g glycemic carbohydrate. These portions were frozen prior to use.

Composition of Test Bars (Data From the Label)

| | Weight (g) | Fat (g) | Protein (g) | Total Carb (g) | Fiber (g) | Maltitol (g) |
|---|---|---|---|---|---|---|
| Endulge Chocolate | 30 | 13 | 1 | 16 | 3 | 11 |
| Endulge Chocolate Peanut | 30 | 13 | 2 | 15 | 3 | 11 |
| Endulge Chocolate Crunch | 30 | 12 | 3 | 15 | 3 | 10 |

Blood samples (2-3 drops each) were collected into 5 ml tubes containing a small amount of sodium fluoride/potassium oxalate, mixed by rotating the tube vigorously, and placed into a refrigerator. After the last blood sample was obtained, subjects were offered a snack and then allowed to leave. Blood samples were then stored at −20° C. prior to analysis of glucose using a YSI analyzer.

Data Analysis

Incremental area under the plasma glucose curves (IAUC) were calculated using the trapezoid rule and ignoring area beneath the baseline (the method used for the glycemic index). The blood glucose concentrations and increments at each time and the IAUC values were subjected to repeated-measures analysis of variance (ANOVA) examining for the effect of test meal. After demonstration of significant heterogeneity, the significance of the differences between individual means was assessed using Tukey's test to adjust for multiple comparisons. The IAUC after 0, 5, 10 and 20 g bread for each subject were regressed on the dose of carbohydrate consumed to develop a dose-response curve. This was used to calculate the IAUC after consuming the same amount of glycemic carbohydrate from bread as the amount of net carbohydrate (total carbohydrate minus dietary fiber) contained in the test bars (either 12 or 13 g). These values were used to calculate the relative glycemic response (RGR) of each test meal. The mean IAUC for all subjects was regressed against the dose of carbohydrate consumed and this regression equation used to calculate how much white bread would have to be consumed to produce an IAUC equal to the mean IAUC after each test bar, i.e. the white bread equivalent.

Results

Subjects Studied

Details of the 4 male and 6 female subjects studied are shown in the table below. One female subject dropped out after the 2$^{nd}$ test because she became pregnant. She was replaced by a male subject.

Dose Response for White Bread

FIG. 4 shows the IAUC after the drink alone and the 3 doses of bread plotted against the amount of glycemic carbohydrate consumed. The plot uses the mean values obtained from the tests. The regression equations and correlation coefficients (r values) are shown below. The r values ranged from 0.613 to 0.995, with 7 of 9 subjects having r>0.95.

| ID | y-intercept | Slope | Correlation Coefficient |
|---|---|---|---|
| 1 | 12.3 | 3.30 | 0.979 |
| 27 | 1.7 | 6.87 | 0.995 |
| 31 | −4.7 | 11.02 | 0.991 |
| 33 | 18.6 | 2.60 | 0.838 |
| 38 | 21.7 | 2.63 | 0.959 |
| 39 | 28.7 | 3.68 | 0.778 |
| 43 | 16.6 | 6.52 | 0.985 |
| 44 | 6.8 | 5.31 | 0.988 |
| 48 | 23.4 | 1.70 | 0.613 |
| 55 | 13.0 | 3.36 | 0.953 |
| Mean | 13.8 | 4.70 | |

Blood Glucose Responses

FIGS. 1 through 4 show the glycemic responses for each test bar, for the drink alone and for the 3 doses of white bread. Blood glucose responses increased linearly. The regression equation of mean IAUC on dose of carbohydrate (d) was: IAUC=4.70d+13.8 (r=0.999).

The average areas under the curve after the Endulge Chocolate, Endulge Chocolate Peanut and Endulge Chocolate Crunch bars did not differ significantly from each other, and were similar or less than the response after 5 g carbohydrate from white bread. The ANOVA indicates that the IAUC values after the drink alone and each dose of white bread differed significantly from each other, and there was no significant difference between the 3 test bars.

Analysis of Variance

An analysis of variance was performed to show the statistical comparisons for palatability, and glucose response at each time point for the different treatments. In each case. Tukey's LSD (least squares deviation) is the least significant difference based on Tukey's test. Means which differ by more than this amount are statistically significantly different.

Palatability: the bars were rated as significantly more palatable than bread, but the palatability ratings of the bars did not differ significantly from each other.

Fasting glucose: there were small but significant differences in fasting glucose before the treatments. Evidence that this does not have an important impact on the interpretation of the results is that the dose-response curve for bread is linear despite the fact that the 0 and 10 g doses had significantly lower fasting glucose than the 5 and 20 g doses.

Postprandial time points: Significant differences between treatments existed at 15, 30, 45, 60, and 120 min. The areas under the glycemic response curve after the 20 g carbohydrate bread dose were significantly greater than that after the 10 g dose, which areas, in turn, were significantly greater than the response to the 5 g dose, which, in turn, were significantly greater than the areas after 0 g bread. The glycemic response areas after the 3 bars were intermediate between the 0 g and 5 g bread doses, and did not differ significantly from each other, nor from the 0 g and 5 g bread responses.

Relative Glycemic Response

The relative glycemic responses for the Endulge Chocolate, Endulge Chocolate Peanut and Endulge Chocolate Crunch bars, respectively, were 39±5, 48±9 and 31±7.

Glycemic Equivalent Amount of Bread

The regression of IAUC after bread on dose of glycemic carbohydrate allows calculation of the amount of bread which produces a given IAUC. This amount is termed the glycemic equivalent. The bread glycemic equivalent for one Endulge Chocolate bar is 3.3±0.8 g glycemic carbohydrate, or approximately 6.6 g of the total weight of the bread, or 0.28 slices (1 slice=24 g). Similarly, the bread glycemic equivalents of Endulge Chocolate Peanut and Endulge Chocolate Crunch bars, respectively, are amounts of bread containing 3.6±1.6 g and 2.6±0.8 g glycemic carbohydrate, or approximately 0.30 and 0.22 slices.

Example 2

The glycemic responses of 1 serving (1 bar=30 g) of Endulge Chocolate Almond Bar, 1 serving (1325 ml can) of Vanilla Shake, 1 slice (28 g) of Atkins' White Bread, 1 slice (28 g) Atkins' Rye Bread, 1 serving of Quick & Easy Pancakes and 1 serving of Quick & Easy Blueberry Muffins were determined in 10 healthy subjects (4 male, 6 female; 36±6 years of age; body mass index 22.8±0.8 kg/m$^2$), relative to the response from white bread. Each subject was studied in the morning after 10-14 h overnight fasts. In addition to a standard drink plus the 6 test products, the glycemic response of each subject was determined after the standard drink alone and the drink plus 5, 10 and 20 g glycemic carbohydrate portions of white bread. The incremental area under the glycemic response curve (IAUC) increased in a linear fashion as the amount of carbohydrate consumed from bread increased from 0 to 20 g, with the correlation coefficient (R) being >0.95 in 6 of the 10 subjects. The regression equation of mean IAUC on dose of carbohydrate (d) was:

$$IAUC = 4.81d + 12.7 (r=0.989)$$

The RGRs of the rye and white breads, vanilla shake, pancake, muffin and chocolate almond bar, respectively, were 88±12, 102±24, 22±8, 98±20, 131±31 and 55±7. The amount of glycemic carbohydrate from regular white bread which would raise blood glucose to the same extent as the 6 test products, respectively, was 2.3±0.6 g, 3.5±0.9 g, 0.3±0.2 g, 3.1±1.1 g, 5.5±2.1 g and 4.5±1.1 g. This is equivalent to about 1-9 g of regular bread or about 1/20 to 3/8 of a slice.

Methods

Subjects

Ten (10) healthy subjects (4 male and 6 female) aged 18-75 years of age were studied.

| ID | Ethnicity | Sex | Age (y) | Height (cm) | Height (in) | Weight (kg) | Weight (lb) | BMI (kg/m$^2$) |
|---|---|---|---|---|---|---|---|---|
| 1 | African-Am | M | 35 | 173.0 | 68.1 | 87.0 | 191.4 | 29.07 |
| 27 | Asian | F | 24 | 170.2 | 67.0 | 57.5 | 126.5 | 19.85 |
| 31 | Caucasian | F | 53 | 162.0 | 63.8 | 58.2 | 128.0 | 22.18 |
| 33 | Caucasian | F | 37 | 165.0 | 65.0 | 58.0 | 127.6 | 21.30 |
| 38 | Caucasian | M | 20 | 187.5 | 73.8 | 90.6 | 199.3 | 25.77 |
| 39 | Caucasian | F | 70 | 161.3 | 63.5 | 54.8 | 120.6 | 21.06 |
| 43 | Caucasian | F | 53 | 167.6 | 66.0 | 64.8 | 142.6 | 23.07 |

-continued

| ID | Ethnicity | Sex | Age (y) | Height (cm) | Height (in) | Weight (kg) | Weight (lb) | BMI (kg/m²) |
|---|---|---|---|---|---|---|---|---|
| 48 | Caucasian | F | 22 | 162.6 | 64.0 | 55.5 | 122.1 | 20.99 |
| 69 | Caucasian | M | 22 | 185.4 | 73.0 | 71.0 | 156.2 | 20.66 |
| 73 | Middle East | M | 21 | 185.4 | 73.0 | 76.0 | 167.2 | 22.11 |
| | | Mean | 35.7 | 172.0 | 67.7 | 67.8 | 148.2 | 22.61 |
| | | SEM | 5.5 | 4.0 | 1.3 | 4.0 | 9.2 | 0.89 |

Protocol

Subjects each underwent 8 treatments in randomized order on separate days, with tests for each subject occurring at approximately weekly intervals, as set forth in Example 1.

The treatments consisted of one serving (1 bar=30 g) of Endulge Chocolate Almond Bar, 1 serving (1325 ml can) of Vanilla Shake, 1 slice (28 g) of Atkins' White Bread, 1 slice (28 g) Atkins' Rye Bread, 1 serving of Quick & Easy Pancakes and 1 g of Quick & Easy Blueberry Muffins, or the standard drink alone (0 g white or an amount of white bread containing 5, 10 or 20 g glycemic carbohydrate.

Quick & Easy Pancakes and Blueberry Muffins were made according to package directions. For the pancakes, 19 eggs, about 150 ml oil and 3⅙ cups water were added to the entire package of pancake mix (19 servings). Pancakes were made from the batter and the total weight of pancakes made was determined. One serving consisted of the total weight divided by 19. Similarly, for the muffins, the entire package contents were mixed with ¾ cup oil, 4 tbsp butter, 3 eggs and 1¼ cups water and the batter divided into 18 muffin cups and baked according to package directions. The total weight of muffins was determined and divided by 18 to determine the single portion weight. Single portions of pancakes and muffins were weighed out, placed into individual zip-lock plastic bags and stored in the freezer prior to use. Individual portions were warmed in a microwave oven on the morning of the test prior to consumption.

Regular bread was baked in a bread maker in loaves containing 50 g glycemic carbohydrate. The ingredients for each loaf (250 ml warm water, 334 g all purpose flour, 7 g sugar, 4 g salt and 6.5 g yeast) were placed into the bread maker according to instructions, and the machine turned on. After the loaf had been made, it was allowed to cool for an hour, and then weighed and after discarding the crust ends, the remainder was divided into portion sizes containing 5, 10 or 20 g glycemic carbohydrate. These portions were frozen prior to use.

Composition of Test Bars (Data From the Label)

| | Weight (g) | Fat (g) | Protein (g) | Total Carb (g) | Fiber (g) |
|---|---|---|---|---|---|
| Atkins Rye Bread | 28 | 2 | 7 | 7 | 4 |
| Atkins White Bread | 28 | 2 | 7 | 7 | 4 |
| Vanilla Shake | 325 ml | 9 | 20 | 4 | 2 |
| Quick & Easy Pancake* | 24 | 1.5 | 13 | 6 | 3 |
| Quick & Easy Blueberry Muffin* | 18 | 0.5 | 6 | 9 | 6 |
| Endulge Chocolate Almond Bar | 30 | 13 | 2 | 14 | 3 |

*Amounts of nutrients are amounts in mix only.

Blood samples (2-3 drops each) were collected into 5 ml tubes containing a small amount of sodium fluoride/potassium oxalate, mixed by rotating the tube vigorously, and placed into a refrigerator. After the last blood sample was obtained, subjects were offered a snack and then allowed to leave. Blood samples were then stored at −20° C. prior to analysis of glucose using a YSI analyzer.

The data were analyzed as set forth in Example 1.

Results

Dose Response for White Bread

Figure 12:
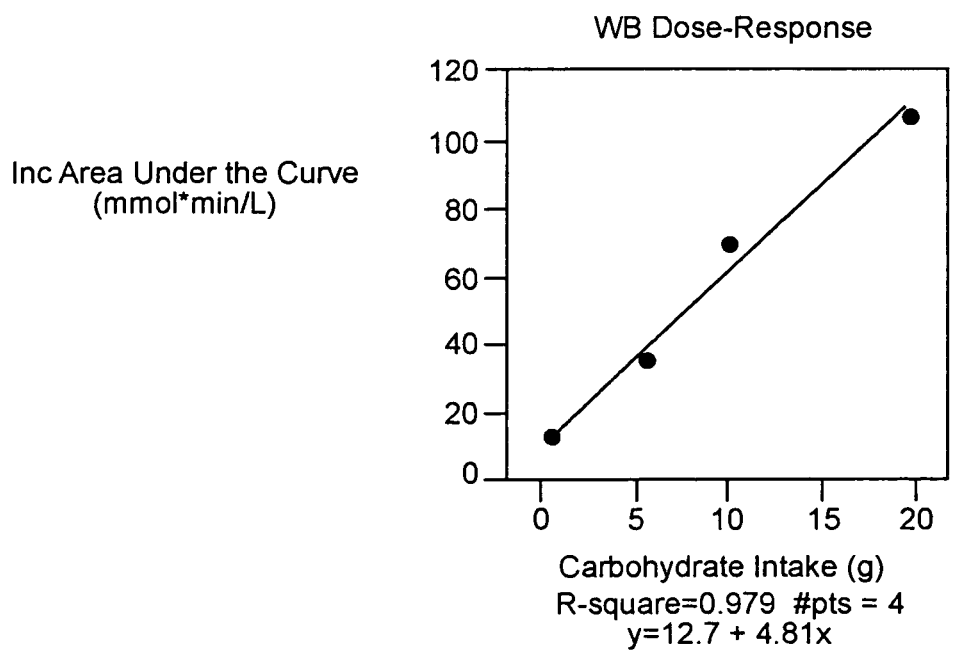
FIG. 12 shows a glycemic response index for white bread loads of below twenty grams of glycemic carbohydrate.
Figure 13:
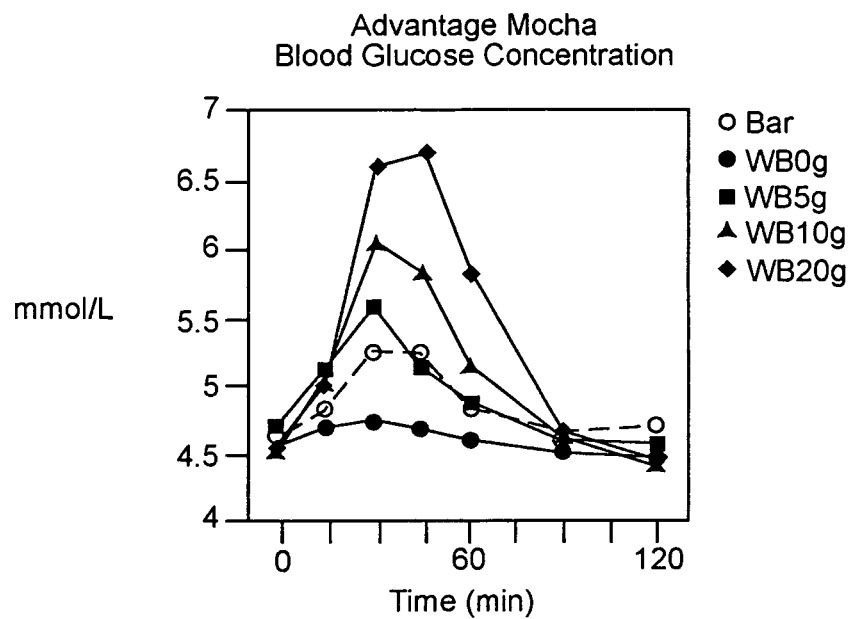
FIG. 13 shows blood glucose response curves for Atkins' Advantage Mocha bar, and white bread at glycemic carbohydrate loads of zero, five, ten and twenty grams.
Figure 14:
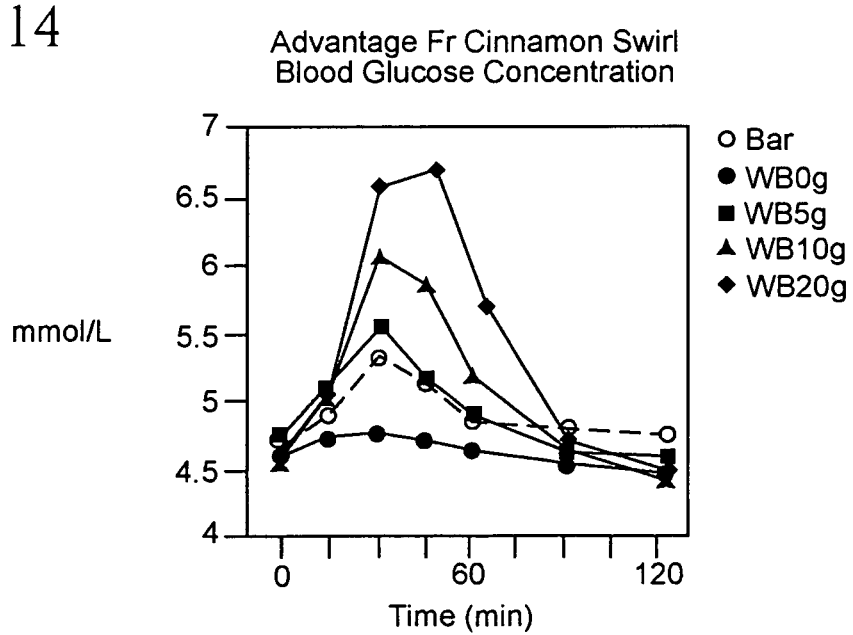
FIG. 14 shows blood glucose response curves for Atkins' Advantage Frosted Cinnamon Swirl bar, and white bread at glycemic carbohydrate loads of zero, five, ten and twenty grams.
Figure 15:
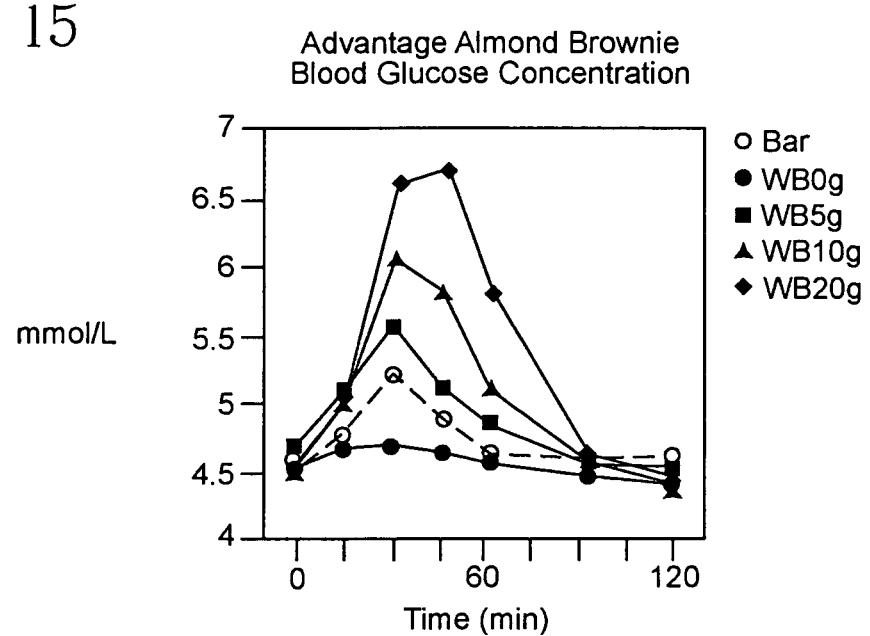
FIG. 15 shows blood glucose response curves for Atkins' Almond Brownie, and white bread at glycemic carbohydrate loads of zero, five, ten and twenty grams.
Figure 16:
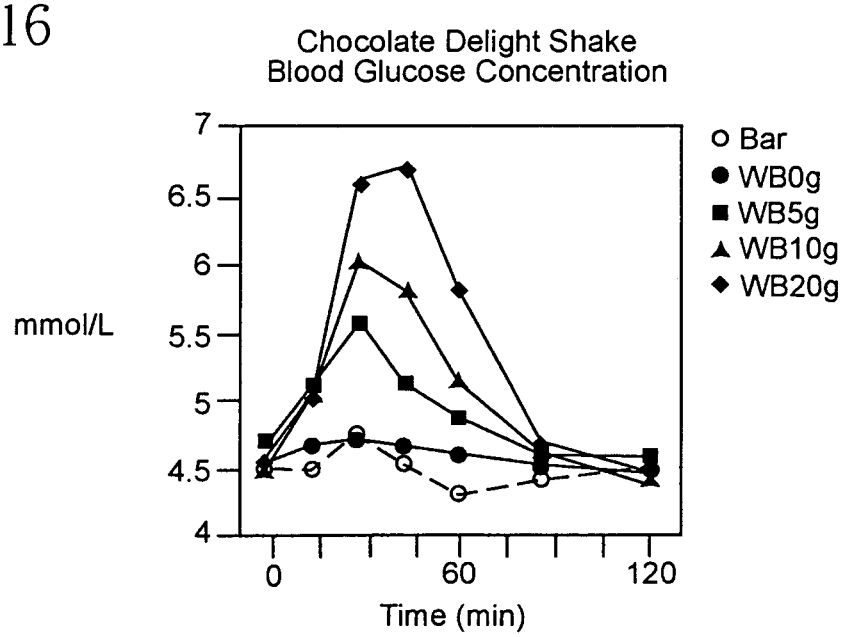
FIG. 16 shows blood glucose response curves for Atkins' Chocolate Delight Shake, and white bread at glycemic carbohydrate loads of zero, five, ten and twenty grams.

FIG. 12 shows the IAUC after the drink alone and the 3 doses of bread plotted against the amount of glycemic carbohydrate consumed. The plot uses the mean values obtained from the tests. The regression equations and correlation coefficients (r values) are shown below. The r values ranged from 0.773 to 0.999, with 6 of 10 subjects having r>0.95.

| ID | y-intercept | Slope | Correlation Coefficient |
|---|---|---|---|
| 1 | 18.2 | 2.83 | 0.996 |
| 27 | 9.84 | 4.65 | 0.950 |
| 31 | −8.83 | 10.53 | 0.978 |
| 33 | 26.1 | 4.14 | 0.913 |
| 38 | 9.63 | 2.62 | 0.935 |
| 39 | 15.5 | 5.47 | 0.969 |
| 43 | 22.1 | 7.67 | 0.983 |
| 48 | 12.6 | 1.64 | 0.848 |
| 69 | 13.2 | 1.70 | 0.773 |
| 73 | 8.65 | 6.79 | 0.999 |
| Mean | 12.7 | 4.8 | |

Blood Glucose Responses

Figure 8:
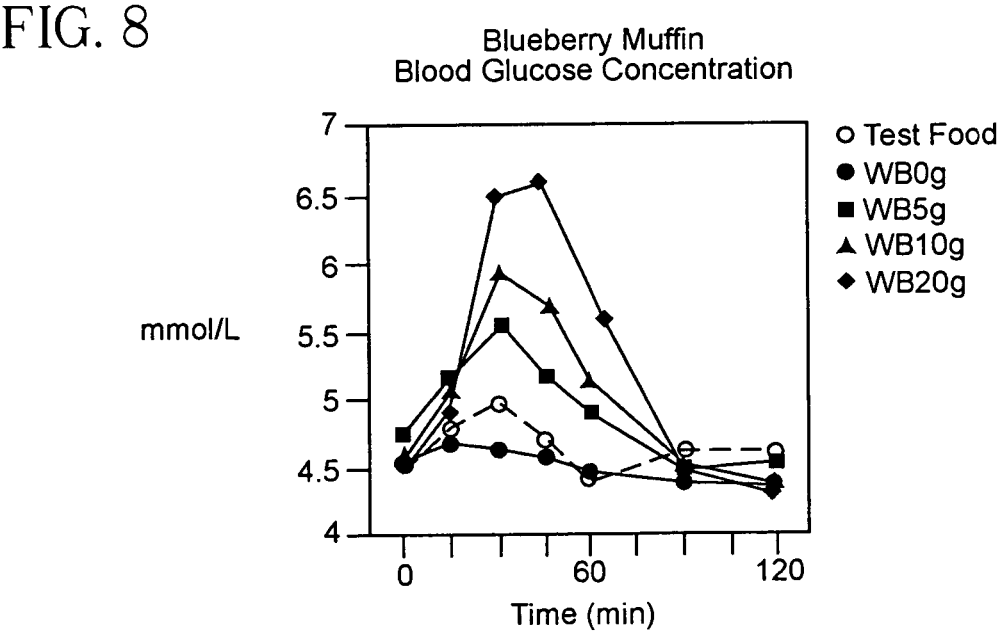
FIG. 8 shows blood glucose response curves for Atkins' Blueberry Muffin, and white bread at glycemic carbohydrate loads of zero, five, ten and twenty grams, with an outlier excluded.
Figure 9:
FIG. 9 shows blood glucose response curves for Atkins' White Bread, and white bread at glycemic carbohydrate loads of zero, five, ten and twenty grams.
Figure 10:
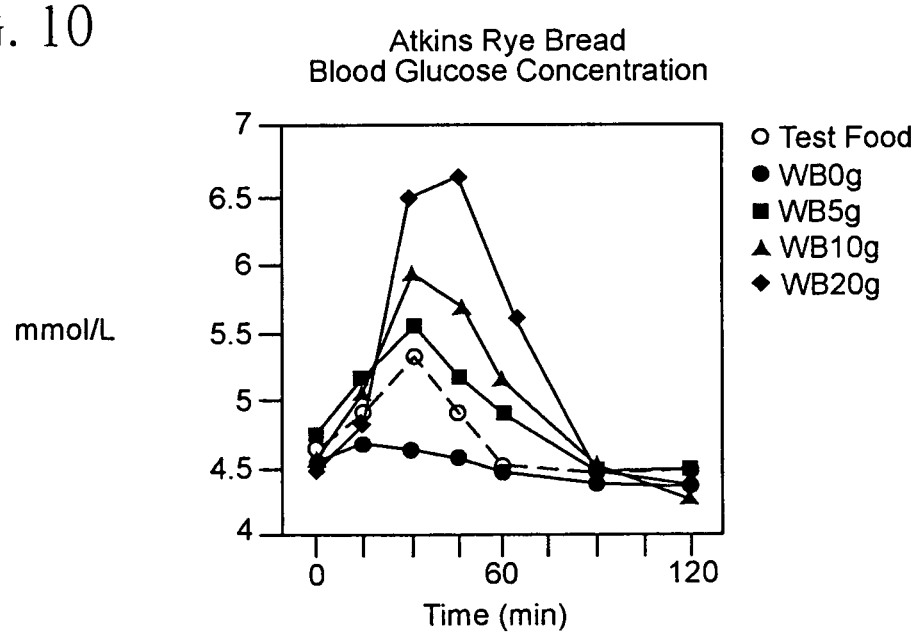
FIG. 10 shows blood glucose response curves for Atkins' Rye Bread, and white bread at glycemic carbohydrate loads of zero, five, ten and twenty grams.
Figure 11:
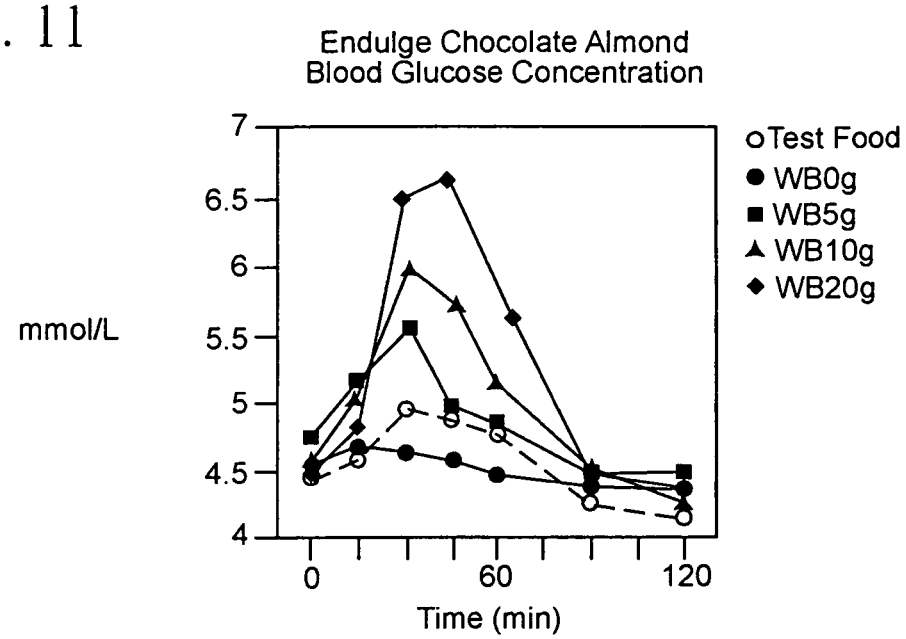
FIG. 11 shows blood glucose response curves for Atkins' Endulge Chocolate Almond, and white bread at glycemic carbohydrate loads of zero, five, ten and twenty grams.

FIGS. 5 through 11 show the glycemic responses for each test food plotted with the response to the drink alone and the 3 doses of white bread. Blood glucose responses increased linearly with an increasing dose of bread ingested. The regression equation of mean IAUC on dose of carbohydrate (d) was: IAUC=4.8d+12.7 (R=0.989). The blood glucose concentration of subject 1 at 90 min after Blueberry Muffin was unexpectedly high at 6.96 mmol/L. This value results in a small peak of blood glucose at 90 min which does not occur for any other food. (See FIG. 7.) The value was checked and verified, but appears to be an outlier. FIG. 8 shows the results with this one outlier removed and replaced by the average value of the blood glucose concentrations at 60 and 120 min. This results in a more "normal" looking glycemic response curve. Nevertheless, all the statistical analysis are based on including the outlying data point.

Analysis of Variance

An analysis of variance was performed as set forth in Example 1.

Palatability: there were significant differences in palatability between the 6 test products and the different doses of white bread. Pancake was significantly less palatable than all the other test meals. The chocolate almond bar was significantly more palatable than the reference white bread at 10 g and the Atkins white bread.

Fasting glucose: there were no significant differences in fasting glucose before the treatments.

Postprandial time points: Significant differences between treatments existed at 15, 30, 45, and 60. The areas under the glycemic response curve after the 20 g carbohydrate bread dose were significantly greater than that after the 10 g dose, which, in turn, were significantly greater than the response to the 5 g dose, which areas, in turn, were significantly greater than the response after 0 g bread. The glycemic response areas after pancake, muffin, Atkins breads and the chocolate almond bar did not differ significantly from each other or from the 5 g dose of bread. The vanilla shake elicited a significantly lower glycemic response than all other test meals except the test containing 0 g bread.

Relative Glycemic Response

The relative glycemic responses (RGR) for Atkins white and rye breads, pancake and muffin were similar to that for the reference bread. The RGR for shake, 22±8, and chocolate almond bar, 55±7, were significantly less than reference bread. When the outlier value from the Blueberry muffin test was removed, there was no significant impact on the RGR, falling from 131±30 to 109±30.

Glycemic Equivalent Amount of Bread

The regression of IAUC after bread on dose of glycemic carbohydrate allows calculation of the amount of bread which produces a given IAUC. The bread glycemic equivalent amounts ranged from 0.3±0.2 g to 5.5±2.1 g, equivalent to about 1-9 g of regular bread or about 1/20 to 3/8 of a slice. Removal of the outlying blood glucose concentration from the blueberry muffin data reduced the bread equivalent from 5.5±2.1 g to 3.8±1.8 g.

Example 3

The glycemic responses of 1 serving (1 bar=60 g) of Advantage Mocha Bar, Advantage Frosted Cinnamon Swirl Bar, and Advantage Almond Brownie bar and 1 serving (1325 ml can) of Chocolate Delight Shake were determined in 10 healthy subjects (4 male, 6 female; 36±6 years of age; body mass index 22.8±0.8 kg/m$^2$), relative to the response from white bread. Each subject was studied on 8 occasions in the morning after 10-14 h overnight fasts. In addition to a standard drink plus the 4 test products, the glycemic response of each subject was determined after the standard drink alone and the drink plus 5, 10 and 20 g glycemic carbohydrate portions of white bread. The incremental area under the glycemic response curve (IAUC) increased in a linear fashion as the amount of carbohydrate consumed from bread increased from 0 to 20 g, with the correlation coefficient (R) being >0.95 in 6 of the 10 subjects. The regression equation of mean IAUC on dose of carbohydrate (d) was:

$$IAUC = 4.86d + 12.3 (r=0.992)$$

The RGR of the mocha, cinnamon swirl and brownie bars and the chocolate shake, respectively, were 40±6, 45±8, 32±4 and 57±23. The amount of glycemic carbohydrate from regular white bread which would raise blood glucose to the same extent as the 4 test products, respectively, was 2.9±1.0 g, 3.2±1.2 g, 2.0±0.8 g, and 0.6±0.4 g. This is equivalent to about 1-6 g of regular bread or about 1/20 to 1/4 of a slice.

Methods

Subjects

Ten (10) healthy subjects (4 male and 6 female) aged 18-75 years of age were studied. The subjects are the same as in Example 2.

Protocol

Subjects each underwent 8 treatments in randomized order on separate days, with tests for each subject occurring at approximately weekly intervals, as set forth in Example 1.

The treatments consisted of one serving (1 bar=60 g) of Advantage Mocha Bar, Advantage Frosted Cinnamon Swirl Bar, and Advantage Almond Brownie Bar or 1 serving (1325 ml can) of Chocolate Delight Shake, or the standard drink alone (0 g white bread), or an amount of white bread containing 5, 10 or 20 g glycemic carbohydrate. The ingredients for each loaf, and methods of preparation, were as set forth in Example 2 for regular bread.

Composition of Test Bars (Data From the Label)

|  | Weight (g) | Fat (g) | Protein (g) | Total Carb (g) | Fiber (g) |
| --- | --- | --- | --- | --- | --- |
| Advantage Mocha Bar | 60 | 10 | 20 | 22 | 10 |
| Advantage Frosted Cinnamon Swirl Bar | 60 | 11 | 19 | 21 | 10 |
| Advantage Almond Brownie Bar | 60 | 8 | 21 | 21 | 7 |
| Chocolate Delight Shake | 325 ml | 9 | 20 | 5 | 3 |

Blood samples were collected, and analyzed as set forth in Example 2. The data were analyzed as set forth in Example 2.

Results

Dose Response for White Bread

Figure 17:
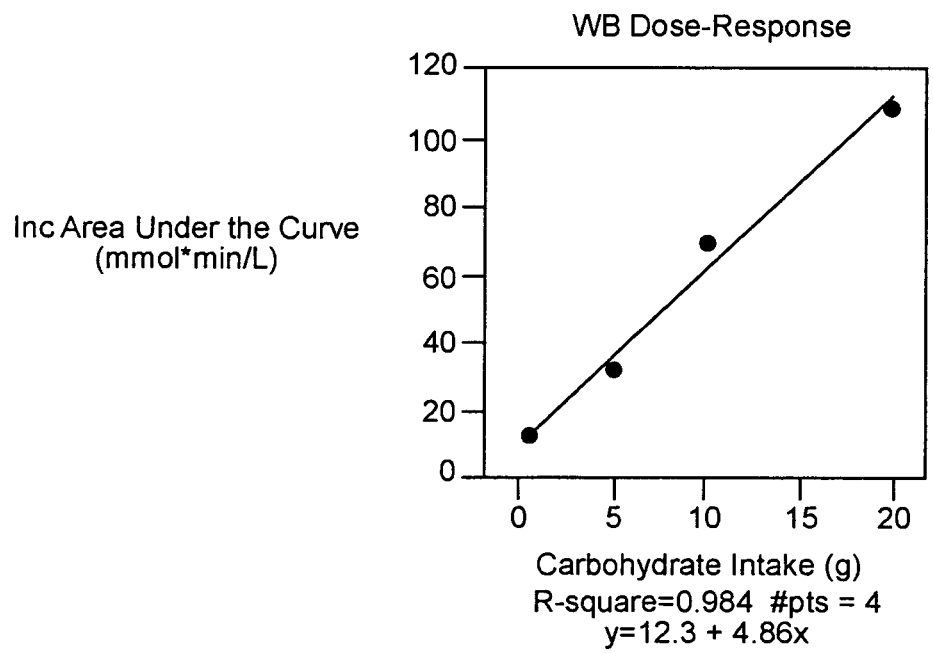
FIG. 17 shows a glycemic response index for white bread loads of below twenty grams of glycemic carbohydrate.

FIG. 17 shows the IAUC for each subject after the drink alone and the 3 doses of bread plotted against the amount of glycemic carbohydrate consumed. The plot uses the mean values obtained from the tests. The regression equations and correlation coefficients (r values) are shown below. The r values ranged from 0.763 to 0.996, with 6 of 10 subjects having r>0.95.

| ID | y-intercept | Slope | Correlation Coefficient |
| --- | --- | --- | --- |
| 1 | 16.3 | 2.78 | 0.992 |
| 27 | 1.03 | 6.91 | 0.995 |
| 31 | −12.4 | 11.43 | 0.988 |
| 33 | 30.6 | 2.98 | 0.802 |
| 38 | 13.2 | 2.47 | 0.857 |
| 39 | 11.3 | 5.65 | 0.982 |
| 43 | 24.0 | 7.55 | 0.985 |
| 48 | 16.2 | 1.75 | 0.763 |
| 69 | 9.2 | 1.59 | 0.949 |
| 73 | 13.9 | 5.45 | 0.996 |
| Mean | 12.3 | 4.9 |  |

Blood Glucose Responses

FIGS. 13 through 16 show the glycemic responses for each test food plotted with the response to the drink alone and the 3 doses of white bread. Blood glucose responses increased linearly with an increasing dose of bread ingested. The regression equation of mean IAUC on dose of carbohydrate (d) was: IAUC=4.9d+12.3 (R=0.992).

Analysis of Variance

An analysis of variance was performed as set forth in Example 1.

Palatability: there were no significant differences in palatability between the 4 test products and the different doses of white bread.

Fasting glucose: there were no significant differences in fasting glucose before the treatments.

Postprandial time points: Significant differences between treatments existed at 15, 30, 45, and 60. The areas under the glycemic response curve after the 20 g carbohydrate bread dose was significantly greater than that after the 10 g dose, which in turn was significantly greater than the response to the 5 g dose, which, in turn, was significantly greater than the response after 0 g bread. The glycemic response areas after the 3 bars did not differ significantly from each other or from the 5 g dose of bread. The mocha and cinnamon bars had glycemic response areas significantly greater than that after 0 g bread, with the difference for brownie bar just missing significance. The glycemic response after each of the 3 bars was significantly less than that after the 10 g bread dose. The glycemic response after chocolate shake was no different from that after 0 g bread, and significantly less than those after the 3 bars and the 5 g bread dose.

Relative Glycemic Response

The relative glycemic responses (RGR) for the mocha, cinnamon and brownie bars, respectively, were 40±6, 45±8 and 32±4. The RGR for chocolate shake was 57±23. The reason for the much greater variability in the RGR value for chocolate shake is that because the amount of carbohydrate in the product, 2 g, is very low, the absolute responses are very low. Thus, the random variation in the glycemic responses become very large when expressed as a ratio.

Glycemic Equivalent Amount of Bread

The regression of IAUC after bread on dose of glycemic carbohydrate allows calculation of the amount of bread which produces a given IAUC for each subject. The bread glycemic equivalent amount one Advantage Mocha bar was 2.9±1.0 g of carbohydrate, or approximately 6 g of bread or 1.27 slices (1 slice=22 g). Similarly, the glycemic equivalents of the Advantage Cinnamon and Almond Brownie, respectively, are amounts of bread containing 3.2±1.2 g and 2.0±0.8 g glycemic carbohydrate, which equals about 6 and 4 g bread, or about 0.3 and 0.2 slices. The chocolate shake has a bread equivalent of only 0.6±0.4 g, which equals about 1 g of bread or about $\frac{1}{20}^{th}$ of a slice.

As can be seen from the above Examples, the glycemic responses elicited by comestibles, such as the bars, are expressed in terms of white bread glycemic carbohydrate equivalents. Additionally, as shown, the glycemic responses are expressed in terms of white bread slice portions.

Thus, while there have been described what are presently believed to be the preferred embodiments of the present invention, other and further embodiments, modifications, and improvements will be known to those skilled in the art, and it is intended to include all such further embodiments, modifications, and improvements and come within the true scope of the claims as set forth below.

We claim:

1. A method for determining a standard comestible Equivalent Glycemic Load of a dietary comestible, the method comprising:
(a) establishing a reliable glycemic response index for a standard comestible, wherein said index correlates standard comestible glycemic response with standard comestible glycemic load, wherein said standard comestible glycemic load is in terms of a uniform unit of said standard comestible;
(b) determining the glycemic response produced by a dietary comestible, and
(c) identifying the standard comestible glycemic load from said index which is correlated with said glycemic response of said dietary comestible, wherein the identified standard comestible glycemic load is the standard comestible Equivalent Glycemic Load of the dietary comestible, wherein the dietary comestible is a manufactured and/or processed comestible.

2. A method according to claim 1 wherein said standard comestible glycemic load is in terms of the total weight of said standard comestible.

3. A method according to claim 1 wherein said index correlates glycemic response with glycemic carbohydrate load at loads below fifty grams.

4. A method according to claim 2 wherein said index correlates glycemic response with glycemic carbohydrate load at loads below thirty-five grams.

5. A method according to claim 2 wherein said index correlates glycemic response with glycemic carbohydrate load at loads below twenty-five grams.

6. A method according to claim 2 wherein said standard comestible Equivalent Glycemic Load is converted into terms of the total weight of said standard comestible.

7. A method according to claim 1 wherein said standard comestible is selected from the group consisting of white bread and glucose.

8. A method according to claim 1 wherein said uniform unit is a slice of white bread.

9. A method according to claim 1 wherein said glycemic responses are determined from capillary glucose levels or plasma glucose levels.

10. A method according to claim 1 wherein said glycemic responses are calculated in terms of incremental area under a blood glucose response curve (IAUC).

11. A method according to claim 10 wherein said IAUC is calculated by evaluating only the incremental area above a baseline wherein said baseline is the glycemic response prior to consumption of said dietary and standard comestibles.

12. A method according to claim 10 wherein said IAUC is calculated by subtracting the incremental area below a baseline from the incremental area above said baseline wherein said baseline is the glycemic response prior to consumption of said dietary and standard comestibles.

13. A method according to claim 1 wherein said dietary comestible is a mixed meal.

14. A method according to claim 10 wherein said index is defined by the following equation: IAUC=m(glycemic carbohydrate load)+b, wherein m is a constant, b is the glycemic response at baseline, and said load is below fifty grams of glycemic carbohydrate.

15. A method of classifying a dietary comestible according to a standard comestible Equivalent Glycemic Load, comprising:
(a) establishing a reliable glycemic response index for a standard comestible, wherein said index correlates standard comestible glycemic response with standard comestible glycemic load, wherein said standard comestible glycemic load is in terms of a uniform unit of said standard comestible;
(b) determining the glycemic response produced by a dietary comestible; and
(c) identifying the standard comestible glycemic load from said index which is correlated with said glycemic response of said dietary comestible, wherein the identified standard comestible glycemic load is the standard comestible Equivalent Glycemic Load of the dietary comestible, whereby said dietary comestible is classified according to a standard comestible Equivalent Glycemic Load, wherein the dietary comestible is a manufactured and/or processed comestible.

16. A method of controlling blood glucose levels in an individual comprising:
(a) identifying a dietary comestible by a standard comestible Equivalent Glycemic Load, comprising:
  (i) establishing a reliable glycemic response index for a standard comestible, wherein said index correlates standard comestible glycemic response with standard comestible glycemic load, wherein said standard comestible glycemic load is in terms of a uniform unit of said standard comestible,
  (ii) determining the glycemic response produced by said dietary comestible, and
  (iii) identifying the standard comestible glycemic load from said index which is correlated with said glycemic response of said dietary comestible, wherein the identified standard comestible glycemic load is the standard comestible Equivalent Glycemic Load of the dietary comestible; and
(b) including a dietary comestible which has a selected standard comestible Equivalent Glycemic Load in the diet of said individual,
whereby the blood glucose levels of said individual is controlled.

17. A computer readable, non-transitory storage medium comprising instructions that when executed by a computing device, cause the computing device to:
(a) establish a reliable glycemic response index for a standard comestible, wherein said index correlates standard comestible glycemic response with standard comestible glycemic load, wherein said standard comestible glycemic load is in terms of a uniform unit of said standard comestible;
(b) determine the glycemic response produced by a dietary comestible, and
(c) identify the standard comestible glycemic load from said index which is correlated with said glycemic response of said dietary comestible, wherein the identified standard comestible glycemic load is the standard comestible Equivalent Glycemic Load of the dietary comestible.

18. A storage medium according to claim 17 wherein said standard comestible glycemic load is in terms of the total weight of said standard comestible.

19. A storage medium according to claim 17 wherein said standard comestible is selected from the group consisting of white bread and glucose.

20. A storage medium according to claim 17 wherein said uniform unit is a slice of white bread.

* * * * *

UNITED STATES PATENT AND TRADEMARK OFFICE
CERTIFICATE OF CORRECTION

PATENT NO. : 8,571,801 B2
APPLICATION NO. : 11/368297
DATED : October 29, 2013
INVENTOR(S) : Anfinsen et al.

Page 1 of 1

It is certified that error appears in the above-identified patent and that said Letters Patent is hereby corrected as shown below:

IN THE SPECIFICATION:

Column 25, line 21:
Now reads: "(0g white or an..."
Should read: -- (0g white bread) or an... --

IN THE CLAIMS:

Claim 4, column 30, line 7:
Now reads: "according to claim 2"
Should read: -- according to claim 1 --

Claim 5, column 30, line 11:
Now reads: "according to claim 2"
Should read: -- according to claim 1 --

Claim 6, column 30, line 14:
Now reads: "according to claim 2"
Should read: -- according to claim 1 --

Signed and Sealed this
Twenty-seventh Day of May, 2014

Michelle K. Lee
*Deputy Director of the United States Patent and Trademark Office*